(12) United States Patent
Nakanishi et al.

(10) Patent No.: US 7,771,709 B2
(45) Date of Patent: Aug. 10, 2010

(54) ALTERNATING COPOLYMER OF ORGANOPOLYSILOXANE WITH GRYCEROL DERIVATIVE AND A COSMETIC COMPRISING THE SAME

(75) Inventors: Tetsuo Nakanishi, Gunma (JP); Toshiki Tanaka, Gunma (JP); Kiyomi Tachibana, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 1799 days.

(21) Appl. No.: 10/883,780

(22) Filed: Jul. 6, 2004

(65) Prior Publication Data

US 2005/0008600 A1    Jan. 13, 2005

(30) Foreign Application Priority Data

| Jul. 7, 2003 | (JP) | 2003-192572 |
| Jul. 9, 2003 | (JP) | 2003-194500 |
| Jun. 28, 2004 | (JP) | 2004-189229 |

(51) Int. Cl.
*A61Q 5/12* (2006.01)
(52) U.S. Cl. ................................. 424/70.12
(58) Field of Classification Search ........................ None
See application file for complete search history.

(56) References Cited

U.S. PATENT DOCUMENTS 4,431,789 A    2/1984   Okazaki et al.
5,472,686 A   12/1995   Tsubaki et al.

FOREIGN PATENT DOCUMENTS

| EP | 0 492 657 A1 | 7/1992 |
| EP | 1 112 733 A1 | 7/2001 |
| JP | 57-149290 A | 9/1982 |
| JP | 62-216635 | * 9/1987 |
| JP | 62-216635 A | 9/1987 |
| JP | 4-211605 A | 8/1992 |
| JP | 4-234307 A | 8/1992 |
| JP | 5-163436 A | 6/1993 |
| JP | 6-157236 A | 6/1994 |
| JP | 9-71504 A | 3/1997 |
| JP | 10-310504 A | 11/1998 |
| JP | 10-310505 A | 11/1998 |
| JP | 10-310506 A | 11/1998 |
| JP | 10-310507 | * 11/1998 |
| JP | 10-310507 A | 11/1998 |
| JP | 10-310508 A | 11/1998 |
| JP | 10-310509 A | 11/1998 |

OTHER PUBLICATIONS

JP 62-216635 (English Abstract only).*
JP 10-310507 (English Abstract only).*

* cited by examiner

*Primary Examiner*—Robert A Wax
*Assistant Examiner*—Jeffrey T Palenik
(74) *Attorney, Agent, or Firm*—Birch, Stewart, Kolasch & Birch, LLP

(57) ABSTRACT

An alternating copolymer comprising a repeating unit of $\alpha,\omega$-organohydrogensiloxane residue (A) and a repeating unit of a glycerol derivative residue (B) having 1 to 11 hydroxyl groups, the copolymer having the number of a repeating unit (AB) of from 2 to 100.

11 Claims, 1 Drawing Sheet

ALTERNATING COPOLYMER OF ORGANOPOLYSILOXANE WITH GRYCEROL DERIVATIVE AND A COSMETIC COMPRISING THE SAME

CROSS REFERENCE

This application claims benefits of Japanese Patent application No. 2003-192572 filed on Jul. 7, 2003, Japanese Patent application No. 2003-194500 filed on Jul. 9, 2003, and Japanese Patent application No. 2004-189229 filed on Jun. 28, 2004, the contents of which are hereby incorporated by reference.

FIELD OF THE INVENTION

This invention relates to an alternating copolymer of organopolysiloxane with glycerol derivative and to a cosmetic comprising the same as an oil agent or an emulsifier.

DESCRIPTION OF THE PRIOR ART

Human secretions such as sweat, tears and sebum cause makeup runs. Especially, in makeup cosmetics, an oil agent contained in cosmetics along with sebum secreted from the skin causes excessive wetting of cosmetic powder, which results in serious makeup runs. In order to reduce the amount of cosmetic oil remaining on the skin, an attempt was made to use a volatile oil such as octamethylcyclotetrasiloxane or decamethylcyclopentasiloxane as a part of the oil ingredients to be added.

Generally, an oily cosmetic has good affinity to skin and durability, but it tends to give a user uncomfortable feeling such as oily, tacky, heavy or thick feeling. To reduce the oiliness, use has been made of a silicone oil which extends well on the skin and gives refreshed feeling. By incorporating the silicone oil, the oiliness is indeed reduced. However, negative properties of the silicone oil such as poor affinity and lack of moisturizing function prevail and the good affinity of an oily cosmetic is lost, too. In addition, satisfactory shiny finish was not obtained.

Although polysiloxanes have good properties as oily agents used for cosmetics, properties concerning feeling are not satisfactory such as affinity with skin, moisturized feeling and dryness.

In makeup cosmetics such as foundation, water repellency has not been improved enough. In skin-care cosmetics such as a milky lotion, an oily agent is desired which has a light feeling, good water repellency, good usability and affinity to the skin.

Meanwhile, a silicone oil obtained by modifying a dimethylpolysiloxane with fluoroalkyl groups described in Japanese Patent Application (JPA) Laid-Open No. 2-295912 has a higher oil repellency than dimethylpolysiloxane.

As the content of the floroalkyl groups increases, the oil repellency increases, but a heavier feeling to the skin occurs. Further, solubility in octamethylcyclotetrasiloxane or decamethylcyclopentasiloxane decreases, which is inconvenient in preparing cosmetic. To get enough solubility, the floroalkyl groups should be decrease, which in turn decrease the oil repellency and the affinity to the skin.

Recently, in a water-in-oil type emulsion (w/o emulsion) composition, a silicone oil is used. Such a w/o emulsion containing the silicone oil is difficult to obtain by using a conventionally used emulsifier such as polyoxyalkylene fatty acid ester.

As a surfactant for the aforesaid w/o emulsion, use of a polyoxyalkylene-modified organopolysiloxane, i.e., polyether-modified silicone which has a good compatibility with a silicone oil is proposed in JPA Laid-Open No. 61-293903, JPA Laid-Open No. 61-293904, JPA Laid-Open No. 62-187406, JPA Laid-Open No. 62-215510, and JPA Laid-Open No. 62-216635.

To prepare an emulsion for a cosmetic application, an ester oil and a hydrocarbon oil are often used together with a silicone oil as a mixture. With the aforesaid polyether-modified silicone, an emulsion of such a mixed oil system is difficult to prepare due to a lack of emulsifying capability of the polyether-modified silicone.

To solve this problem, it is proposed in JPA Laid-Open No. 61-90732 to use the following organopolysiloxane as an emulsifier which has a long alkyl chain and a polyoxyalkylene group.

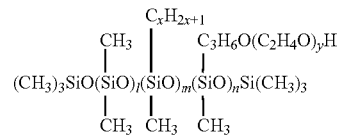

The above organopolysiloxane compound is a good emulsifier for a mixed oil system containing relatively large amount of ester oil or hydrocarbon oil, but not good enough to prepare a stable emulsion of a system containing relatively large amount of silicone oil.

As shown in the formula (5), in an organopolysiloxane compound having a polyoxyalkylene group, the polyoxyalkylene group is usually grafted to the organopolysiloxane chain. Other type of organopolysiloxane is known which has a polyoxyalkylene group (A) bonded to one or both terminals of a siloxane residue (B) to form (AB) type or (ABA) type organopolysiloxane. In Japanese Patents No. 3061434, No. 3071222, and No. 3283277, an organopolysiloxane having a repeating unit of (AB) is disclosed. It is described that the organopolysiloxane functions as an antistatic agent, which is attributed to the polyalkylene group, and can be used for skin cosmetics as well as hair cosmetics.

In an application of a skin cleaning agent, cleaning of makeup cosmetics containing large amount of solid oil such as a lipstick, foundation, eye shadow, eyeliner, and mascara is an issue. A cleaning agent comprising an ordinary soap cannot clean these cosmetic completely, because the soap cannot (dissolve or emulsify the solid oil.

To clean such oily cosmetics, a cleaning agent mainly composed of an oily material has been used. However, such cleaning agent is not enough to clean a makeup cosmetic designed to give a durable and long lasting makeup or the one containing cyclic silicones or a film forming polymer intended to be used in summer when people sweat a lot. In a hair cosmetic, a highly polymerized silicone or a polymer having a high film forming capability is used to protect hair, to add hair bounce or smooth feeling.

To clean such a durable makeup or film forming polymer on hair, a cleaning agent containing a nonionic surfactant or a polyethe-modified silicone is used. However, as film forming capability increases, a cleaning agent having a higher cleaning capability is desired.

Meanwhile, various kinds of glycerol-modified silicones have been reported to solve poor moisturization property and affinity to the skin.

For example, glycerol-modified silicones are described in JPA Laid-Open No. 6-157236, JPA Laid-Open No. 9-71504 and JP Kokoku No. 62-34039; glycerol- and fluoroalkyl-modified silicones in JPA Laid-Open No. 10-310504, No. 10-310505, No. 10-310506, No. 10-310507, No. 10-310508, and No. 10-310509; monoglycerol-modified silicones and a cosmetic comprising the same in Japanese Patent Publication (JP) No. 2613124, JP No. 2844453, JP Kokoku No. 8-22811, JP No. 2587797, and JP No. 2601738. All of the glycerol-modified silicones are intended to suppress drying property of the silicone and tackiness of glycerol.

As a silicone modified with a compound having hydroxyl groups, a polyalcohol-modified silicone is also known wherein the polyalcohol is sucrose or polysacharide. In JP No. 3172787, a modified silicone having a sucrose residue is described and its application as an emulsifier is described in JP No. 3229396, JPA Laid-Open No. 7-41414, and Laid-Open No. 7-41416.

All of the modified silicones are intended to suppress drying property of the silicone with the polyalcohol including glycerol and to suppress tackiness of glycerol with the silicone.

The aforesaid known glycerol-modified silicones are superior to a conventional polyether-modified silicone in that they do not get viscous or show tackiness when mixed with water. However, one drawback with the glycerol-modified silicones is an availability of a raw material polyglycerol having reactive functional groups such as an aliphatic unsaturated group to be reacted with a silicone. For example, in preparing a glycerol-modified silicone by reacting the glycerol derivative compound represented by the formula below with an SiH bond of a silicone, miscibility of the compound with the silicone and hence a reaction rate significantly decrease with increasing the repetition number of "d", due to increasing viscosity and hyrdophilicity of the glycerol derivative.

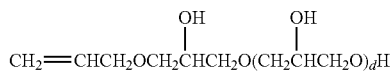

To avoid such decrease in the reaction rate, a large amount of a reaction solvent is required, which decreases yield per volume and hence cost performance. Said problem of poor miscibility is critical in modification of a silicone with a polyglycerol having higher degree of polymerization. Generally, modification with a polyglycerol having a molecular weight over 5,000 is very difficult. Particularly, in modifying the silicone with a small amount of polyglycerol derivative, the polyglycerol derivative tends to exist in a separate phase from the silicone or precipitates, making a reaction product cloudy.

Another drawback is that a hydroxyl group in a polyglycerol having an aliphatic unsaturated group tends to react with SiH group to hinder the addition reaction of the unsaturated group with SiH group and decrease a shelf life of the modified-silicone product.

Such dehydrogenation reaction of SiH with OH group can be suppressed by reacting α,ω-organohydrogensiloxane, which has a higher reactivity in the addition reaction, with a glycerol derivative having one aliphatic unsaturated bond. However, it cannot prevent a reaction product from being cloudy. To prepare a glycerol-modified silicone with a higher molecular weight, a polyglycerol with a higher molecular weight is required, because reaction sites of α,ω-organohydrogensiloxane are limited to the terminals. Such a high molecular weight polyglycerol is less miscible with the siloxane.

By using the triglycerol of the formula below with its OH groups being blocked, the dehydrogenation can be avoided. However, to release the blocking group after the reaction with a silicone, very severe reaction conditions are required, which causes a scission of the silicone chain, so that desired reaction product may not be obtained reproducibly.

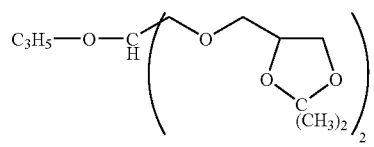

Thus, a purpose of the present invention is to provide a glycerol-modified silicone having a good compatibility with oil agents conventionally used for a cosmetic and a good emulsifying activity to be advantageously used for a cosmetic and to provide a method of producing the same without the aforesaid problems in producing a glycerol-modified silicone.

SUMMARY OF THE INVENTION

As the result of extensive studies, the present inventors have found that a polyglycerol-modified silicone having a higher molecular weight than a conventional one can be obtained, without getting the polyglycerol-modified silicone cloudy, by subjecting α,ω-organohydrogensiloxane and a glycerol derivative to an alternating addition reaction, which glycerol derivative has a relatively low molecular weight and an aliphatic unsaturated group at both terminals. In addition, it has been found that polyglycerol-modified silicones with various contents of glycerol can be prepared by varying a ratio of a degree of polymerization of the siloxane to that of the polyglycerol.

Thus, the present invention is an alternating copolymer comprising a repeating unit of α,ω-organohydrogensiloxane residue (A) and a repeating unit of a glycerol derivative residue (B) having 1 to 11 hydroxyl groups, the copolymer having the number of a repeating unit (AB) of from 2 to 100.

Another aspect of the present invention is a process for preparing the aforesaid alternating copolymer comprising a step of reacting α,ω-organohydrogensiloxane having an SiH bond at both terminals with a glycerol derivative having an aliphatic unsaturated bond at both terminals.

The alternating copolymer of the present invention is clear, and a cosmetic comprising the copolymer has a reduced tackiness, while maintaining affinity to the skin, light spreadability on the skin to give a moisturized sensation. The applied cosmetic on the skin is durable and has a shiny finish of an expensive-looking.

A cosmetic comprising the alternating copolymer of the present invention as an emulsifier is very stable and the quality thereof does not change with temperature change or passage of time.

Moreover, the alternating copolymer may be added to a paint to prevent blocking or to improve flatness, smoothness and abrasion resistance of an applied paint.

PREFERRED EMBODIMENT OF THE INVENTION

Figure 1:
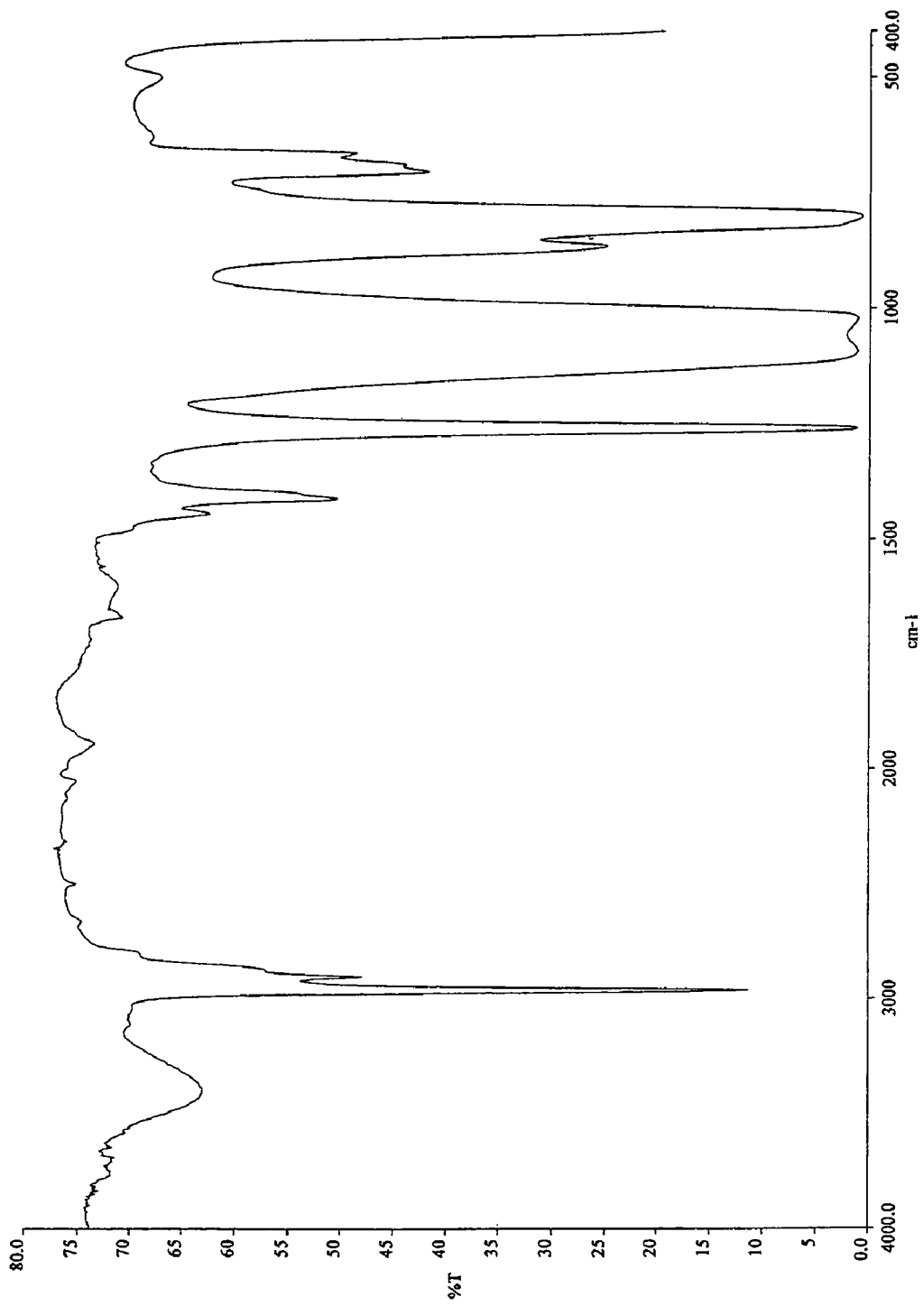
FIG. 1 is an IR chart of the present alternating copolymer 5 prepared in the example 5.

The present copolymer is an alternating copolymer comprising a repeating unit of α,ω-organohydrogensiloxane residue (A) and a repeating unit of a glycerol derivative residue (B) having 1 to 11 hydroxyl groups. The silicone, α,ω-organohydrogensiloxane, is an organopolysiloxane having a hydrogen atom at both terminals. The glycerol derivative residue (B) has one hydroxyl group when the glycerol derivative is monoglycerol derivative, or 2 to 11, preferably 2 to 5, and more preferably 2 to 4 hydroxyl groups when the glycerol derivative is polyglycerol derivative. It is considered, without intending to limit the invention, that the alternating locations of the residue (A) with residue (B) is one of the reasons for the clearness, good emulsifying activity and miscibility with an oily agent. The number of the repeating unit (AB) ranges from 2 to 100, preferably 3 to 30, from the viewpoints of fluidity and solubility at room temperature.

Preferably, the repeating unit (AB) is represented by the following formula (1).

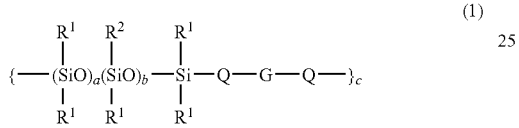
(1)

wherein, $R^1$ may be the same or different and is a group having 1 to 10 carbon atoms selected from the group consisting of alkyl, aryl, aralkyl, amino-substituted alkyl, and carboxyl-substituted alkyl groups, a part of which hydrogen atoms may be replaced with halogen atoms, $R^2$ may be the same or different and is an alkyl group having 11 to 30 carbon atoms, a part of which hydrogen atoms may be replaced with halogen atoms, Q is a divalent organic group having 3 to 20 carbon atoms and may comprise an ether bond and/or an ester bond, G is a mono- or poly-glycerol residue, a is an integer of from 2 to 100, b is an integer of from 0 to 100, and c is an integer of from 2 to 100.

In formula (1), $R^1$ and $R^2$ are monovalent organic functional groups which do not have an aliphatic unsaturated bond. $R^1$ may be the same or different and is a group having 1 to 10 carbon atoms selected from the group consisting of alkyl, aryl, aralkyl, amino-substituted alkyl, and carboxyl-substituted alkyl, part of which hydrogen atoms may be replaced with halogen atoms. Examples of $R^1$ include alkyl groups such as methyl, ethyl, propyl, butyl, pentyl, hexyl, heptyl, octyl, nonyl, and decyl groups; cycloalkyl groups such as cyclopentyl and cyclohexyl groups; aryl groups such as phenyl and tolyl groups; aralkyl groups such as benzyl and phenetyl groups; amino-alkyl groups such as 3-aminopropyl, and 3-[(2-aminoethyl)amino]propyl group; carboxyl-substituted alkyl group such as 3-carboxylpropyl group; and trifluoropropyl and nonafluorooctyl groups.

$R^2$ may be the same or different and is an alkyl group having 11 to 30 carbon atoms part of which hydrogen atoms maybe replaced with halogen atoms, such as undecyl, dodecyl, tridecyl, tetradecyl, hexadecyl, octadecyl, behenyl and partly fluorinated alkyl groups.

In formula (1), Q is a divalent organic group having 3 to 20 carbon atoms and may comprise an ether bond and/or an ester bond such as —$(CH_2)_2$—, —$(CH_2)_3$—, —$CH_2CH(CH_3)CH_2$—, —$(CH_2)_4$—, —$(CH_2)_5$—, —$(CH_2)_6$—, —$(CH_2)_7$—, —$(CH_2)_8$—, —$(CH_2)_2$—$CH(CH_2CH_2CH_3)$—, —$CH_2$—$CH(CH_2CH_3)$—, —$(CH_2)_3$—O—$(CH_2)_2$—, —$(CH_2)_3$—O—$(CH_2)_2$—O—$(CH_2)_2$—, —$(CH_2)_3$—O—$CH_2CH(CH_3)$—, and —$CH_2$—$CH(CH_3)$—$COO(CH_2)_2$—, among which —$(CH_2)_3$— is preferred.

In formula (1), G is a mono- or poly-glycerol residue. Typically, G may have a following chemical structure of (2), (3) or (4). In these formula, s, t, u, and v are integers of from 0 to 10. Examples of G include residue of monoglycerol, diglycerol, triglycerol, tetraglycerol, octaglycerol, decaglycerol, hexadecaglycerol, and octadecaglycerol. A part of hydroxyl groups may be replaced with alkoxyl groups or ester groups.

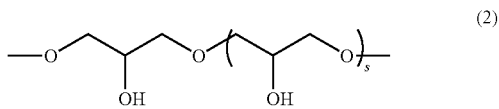
(2)

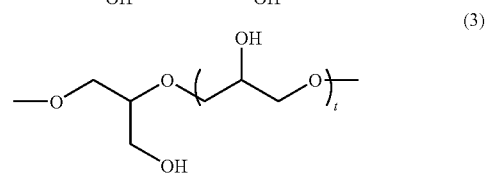
(3)

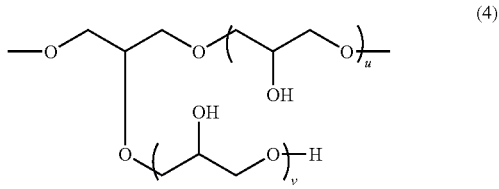
(4)

Preferably, s, t, u, and v are integers of from 1 to 9, and more preferably s, t, and u+v are integers of from 1 to 4.

Referring back to formula (1), a is an integer of from 2 to 100, preferably, from 10 to 60 and b is an integer of from 0 to 100. Preferably, b is 10 to 50% of a, that is from 1 to 50, in order for the alternating copolymer to be miscible with both a silicone oil and an ester oil. In formula (1), c is an integer of from 2 to 100, preferably, from 3 to 30. If c is larger than said upper limit, a copolymer may be too viscous to handle easily. A copolymer with c being smaller than said lower limit may not give a stable emulsion.

The present alternating copolymer can be prepared by subjecting the α,ω-orgnohydrogenpolysiloxane of the formula (5) shown below and mono- or polyglycerol derivative to an addition reaction in the presence of a platinum or rhodium catalyst, which mono- or polyglycerol derivative has an unsaturated group at both terminals, for example, triglycerol dially ether of the formula (i) or (ii).

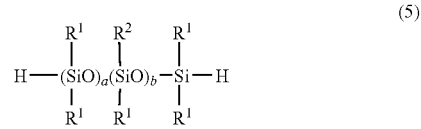
(5)

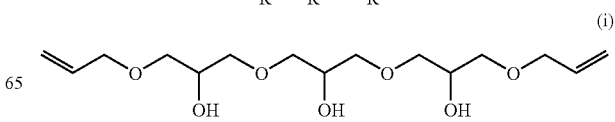
(i)

-continued

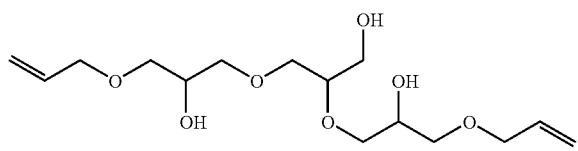
(ii)

Triglycerol diallyl ether of the formula (i) or (ii) may be prepared by adding 2 molar allylglycidyl ether dropwise to 1 molar triglycerol and subjecting the mixture to an addition reaction. Preferably, the reaction is carried out at a temperature of 60 to 120 degrees C. After the reaction, the catalyst is neutralized and, then, volatile substances having a lower boiling point than that of triglycerol diallyl ether are removed by distillation.

Triglycerol diallyl ether thus obtained is considered to be a mixture of the compounds of the formulae (i) and (ii) which is typically a pale yellow liquid having a viscosity of 330 $mm^2$/s, hydroxyl number of 523 KOH mg/g, unsaturation of 6.13 meq/g. The hydroxyl number and unsaturation are nearly equal to theoretical values of 525 and 6.24, respectively, indicating that the diallyl ether obtained by the aforesaid method has two unsaturated groups per molecule.

A diallyl ether with a higher molecular weight can be prepared in the same manner as described above, by using diglycerol or triglycerol in place of glycerol.

A ratio of $\alpha,\omega$orgnohydrogenpolysiloxane of the formula (5) and the polyglycerol diallyl ether of the formula (i) and/or (ii) is such that a molar ratio of SiH group of the $\alpha,\omega$-orgnohydrogenpolysiloxane to CH=$CH_2$ group of the polyglycerol diallyl ether, SiH/CH=$CH_2$, is equal to or greater than 0.5 and smaller than 1.5, preferably equal to or greater than 0.8 and smaller than 1.2.

The aforesaid addition reaction is preferably carried out in the presence of a platinum or rhodium catalyst. Preferred catalysts are chloroplatinic acid, alcohol-modified chloroplatinic acid, and chloroplatinic acid-vinyl siloxane complex.

The amount of the catalyst may be an effective amount, but 500 ppm or less, particularly, 20 ppm or less as platinum or rhodium are preferred. The aforesaid addition reaction may be carried out in an organic solvent if necessary. Examples of the organic solvent include aliphatic alcohols such as methanol, ethanol, 2-propanol, and butanol; aromatic hydrocarbons such as toluene and xylene; aliphatic or alicyclic hydrocarbons such as n-pentane, n-hexane, and cyclohexane; and halogenated hydrocarbons such as dichloromethane, chloroform, and carbon tetrachloride. When such solvent is used, the addition reaction is preferably carried out for 1 to 10 hours while refluxing the solvent.

After the addition reaction, unreacted allyl ether group may be killed by hydrogenation, or alkylation to reduce odor. An antioxidant such as tocopherol or BHT may be added to the copolymer.

The present alternating copolymer may be suitably used as an emulsifier or an oil agent in various products for external application, for example, cosmetics such as emulsified products like milky lotions; makeup products such as lipsticks and oily foundation; skin-care products; hair care products; and drugs for external application.

In the cosmetic, the present copolymer may be incorporated in an amount of from 0.1 to 70 wt %, preferably from 1 to 50 wt % relative to a total weight of the cosmetic.

In the cosmetic, commonly used oil agent, in addition to the present copolymer, may be incorporated which may be solid, semi-solid, or liquid, at an ambient temperature. Examples of the oil agent include natural fats, oils from animals or plants and semi-synthetic oils, such as avocado oil, linseed oil, almond oil, Ibota wax, perilla oil, olive oil, cacao butter, kapok wax, kaya oil, carnauba wax, Glycyrrhiza oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, squalane, olive squalane, squalene, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methyl ester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, POE lanolin alcohol ether, POE lanolin alcohol acetate, lanolin fatty acid polyethylene glycol, POE hydrogenated lanolin alcohol ether, and egg yolk oil. The term "POE" means polyoxyethylene.

The oil agent may be a hydrocarbon oil such as linear, branched and volatile hydrocarbons. Examples include α-olefin oligomers, light isoparaffin, light liquid isoparaffin, ozokerite, synthetic squalane, vegetable squalane, ceresin, paraffin, paraffin wax, polyethylene wax, polyethylene-polypropylene wax, liquid paraffin, pristane, polyisobutylene, microcrystalline wax, and Vaseline.

The oil agent may be a higher fatty acid such as lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

The oil agent may be a higher alcohol such as lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol).

The oil agent may be an ester oil such as diisobutyl adipate, 2-hexyldecyl adipate, di-2-heptylundecyl adipate, isononyl isononate, isotridecyl isononate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate; and a glyceride oil, for example, acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristate isostearate.

The oil agent may be a silicone oil, for example, a linear organopolysiloxane having a low to high viscosity such as dimethylpolysiloxane, methylphenylpolysiloxane, methylhydrogenpolysiloxane, dimethylsiloxane/methylphenylsiloxane copolymer; a cyclic siloxane such as octamethylcyclotetrasiloxane, decamethylcyclopentasiloxane, dodecamethylcyclohexasiloxane, tetramethyltetrahydrogencyclotetrasiloxane, tetramethyltetraphenylcyclotetrasiloxane, tetramethyltetratrifluoropropylsiloxane, and pentamethylpentatrifluoropropylsiloxane; a branched siloxane such as trimethylsiloxymethylsiloxane, tristrimethylsiloxysilane, tetrakistrimethylsiloxysilane, tristrimethylsiloxyphenylsilane; silicone gum such as gummy dimethylpolysiloxane having a high degree of polymerization, gummy dimethylsiloxane/methylphenylsiloxane copolymer and a solution thereof in a cyclic siloxane; trimethylsiloxysilicate and a solution thereof in a cyclic siloxane; a higher alkoxy-modified silicone such as stearoxy silicone; a higher fatty acid-modified silicone alkyl-modified silicone, amino-modified silicone, and fluorine-modified silicone.

The oil agent may be a fluorinated oil such as perfluoropolyethers, perfluorodecaline, and perfluorooctane.

These oil agents may be incorporated in the cosmetic in an amount of from 1 to 99 wt % based on a total weight of the cosmetic.

The cosmetics of the present invention may further comprise one or more of a compound having alcoholic hydroxyl group besides the copolymer of the present invention and the higher alcohol mentioned above. Examples of the compound having alcoholic hydroxyl group include lower monoalcohols such as ethanol and isopropanol; sugar alcohols such as sorbitol and maltose; sterols such as cholesterol, sitosterol, phytosterol, and lanosterol; polyalcohols such as butylene glycol, propylene glycol, butylene glycol, and pentyl glycol. The compound may be incorporated in the cosmetic in an amount of from 0.1 to 98 wt % based on a total weight of the cosmetic.

The cosmetics of the present invention may comprise one or more water-soluble or water-swelling polymer. Examples of the water-soluble or water-swelling polymer include plant polymers such as gum Arabic, tragacanth gum, arabinogalactan, locust bean gum (carob gum), guar gum, karaya gum, carrageenan, pectin, agar, quince seed (i.e., marmelo), starch from rice, corn, potato or wheat, algae colloid, trant gum and locust bean gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, and carboxyvinyl polymer; polyoxyethylene polymers; polyoxyethylene/polyoxypropylene copolymers; acrylic polymers such as sodium polyacrylate, polyethyl acrylate, and polyacrylamide; synthetic water-soluble polymers such as polyethyleneimine and other kind of cationic polymers; semi-synthetic water-soluble polymers such as silicone-modified pulllan; and water-soluble inorganic polymers such as, bentonite, aluminum magnesium silicate, montmorillonite, beidellite, notronite, saponite, hectorite, and silicic anhydride. The examples of the water-soluble polymer further include film forming agents such as polyvinyl alcohol and polyvinyl pyrrolidone. The water-soluble or water-swelling polymer may be incorporated in the cosmetic in an amount of from 0.01 to 25 wt % based on a total weight of the cosmetic.

The present cosmetic may further comprise water, mineral water, seawater, deep-sea water, and rose water according to a purpose of the cosmetic. The water may be incorporated in an amount of from 1 to 99 wt % based on a total weight of the cosmetic.

The present cosmetic may further comprise any powder and coloring agents which are commonly used in cosmetics may be used in the present invention, regardless of the shape (spherical, rod-like, acicular, tubular, irregular, scaly or spindle forms), particle size (size of fume, fine particles or pigment grade), and particle structure (porous and non-porous), such as, for example, inorganic powder, organic powder, surface activating metal salt powder, colored pigments, nacreous pigments, metallic powder pigments, and natural dyes.

Specific examples of the inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectolitre, zeolite, ceramics powder, calcium secondary phosphate, alumina, aluminum hydroxide, boron nitride, and silica.

Examples of the organic powders include polyamide powder, polyester powder, polyethylene powder, polypropylene powder, polystyrene powder, polyurethane, benzoguanamine powder, polymethylbenzoguanamine powder, tetrafluoroethylene powder, polymethylmethacrylate powder, cellulose, silk powder, nylon powder such as Nylon 12 and Nylon 6, spherical silicone elastomer powder having crosslinked dimethylsilicone structure (see Japanese Laid-Open Patent Application No. 3-93834), spherical polymethylsilsesquioxane powder (see Japanese Laid-Open Patent Application No. 3-47848), spherical silicone elastomer powder with its surface coated with polymethylsilsesquioxane (see Japanese Laid-Open Patent Application No. 7-196815) styrene/acrylic acid copolymer, divinylbenzene/styrene copolymer, vinyl resin, urea resin, phenol resin, fluororesin, acrylic resin, melamine resin, epoxy resin, polycarbonate resin, microcrystalline fiber powder, starch powder, and lauroyl lysine.

Examples of the surface activating metal salt powders (metal soaps) include zinc stearate, aluminum stearate, calcium stearate, magnesium stearate, zinc myristate, magnesium myristate, zinc cetyl phosphate, calcium cetyl phosphate, and zinc/sodium cetyl phosphate.

Examples of the colored pigments include inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural dyes, and synthetic resin powder complexes thereof.

Examples of the nacreous pigments include titanium oxide-coated mica, bismuth oxychloride, titanium oxide-coated bismuth oxychloride, titanium oxide-coated talc, fish scales, and titanium oxide-coated colored mica and examples of metallic powder pigments include aluminum powder, copper powder and stainless steel powder.

Examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Examples of the natural dyes include carminic acid, laccaic acid, carthamin, brazilin, and crocin.

Powders which absorb or scatter UV ray may be used, too, such as titanium oxide fine powder, fine powder of titanium oxide containing iron, zinc oxide fine powder, cerium oxide fine powder and a mixture thereof.

These powders can be subjected to compounding or surface treatment with common oil agents, conventional silicone oils, fluorine-containing compounds or surfactants prior to use, as far as such treatment does not adversely affect the present cosmetic. If necessary, two or more powders may be used.

The present cosmetic may further comprise one or more or surfactant. The surfactant may be anionic, cationic, non-ionic or amphoteric. There is not any particular limitation and any surfactant that can be used in common cosmetics may be used.

Examples of the anionic surfactants include fatty acid soaps, such as sodium stearate and triethanolamine palmitate, alkylether carboxylic acids and salts thereof, salts of amino acids and fatty acids, alkylsulfonic acids, alkenesulfonates, sulfonates of fatty acid esters, sulfonates of fatty acid amides, sulfonates of alkylsulfonate-formalin condensates, alkylsulfates, sulfates of secondary higher alcohols, alkyl/allyl ether sulfates, sulfates of fatty acid esters, sulfates of fatty acid alkylolamides, and sulfates of Turkey Red oil, alkyl phosphates, ether phosphates, alkylallylether phosphates, amide phosphates, and N-acylamino surfactants.

Examples of the cationic surfactants include amine salts such as salts of alkylamine, polyamine and amino alcohol fatty acid derivatives, alkyl quaternary ammonium salts, aromatic quaternary ammonium salts, pyridium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkylethers, polyoxypropylene alkylethers, polyoxyethylene alkylphenylether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanolether, polyoxyethylene phytosterolether, polyoxyethylene cholestanolether, polyoxyethylene cholesterylether, polyoxyalkylene-modifed organopolysiloxane (see Japanese Patent No. 2137062 and Japanese Laid-open Patent Application No. 7-330907), polyglycerin-modified organopolysiloxane (Japanese Laid-open Patent Application No. 62-34039, and Japanese Patent Application Nos. 2613124, 2844453, and 2002-179798), polyoxyalkylene/alkyl co-modified-organopolysiloxane (Japanese Laid-open Patent Nos. 61-90732 and 9-59386) alknolamide, sugar ethers, and sugar amides.

Examples of the amphoteric surfactants include betaine, aminocarboxylates, and imidazoline derivatives. A desirable amount of the surfactant to be added ranges from 0.1 to 20 wt %, preferably from 0.2 to 10 wt %, relative to a total weight of the cosmetic.

The present cosmetic may further comprise one or more of a crosslinked organopolysiloxane. Preferably, the crosslinked organopolysiloxane is swelled with a silicone having a viscosity of from 0.65 to 100.0 $mm^2$/sec in a larger amount by weight than the amount of the crosslinked organopolysiloxane itself. This crosslinked organopolysiloxane can be obtained by reacting a SiH bond of organohydrogenpolysiloxane with crosslinking agent having reactive vinylic unsaturated group at molecular terminal. Further, the crosslinked organopolysiloxane may have at least one residue selected from the group consisting of polyoxyalkylene residue, alkyl residue, aryl residue, and fluoroalkyl residue. Examples of the crosslinked organopolysiloxane, though not limited to these, include KSG-15, KSG-16, KSG-18, KSG-210, and KSG-710, all of which are in a gel from swelled with a silicone oil and commercially available from Shin-Etsu Chemical Co.

The crosslinked organopolysiloxane swelled with an oil agent other than the silicone having a viscosity of from 0.65 to 100.0 $mm^2$/sec may be used, too. Examples of such crosslinked organopolysiloxane, though not limited to these, include KSG-310, KSG-320, KSG-330, KSG-340, KSG-41, KSG-42, KSG-43, KSG-44, KSG-810, KSG-820, KSG-830, and KSG-840, all of which are in a gel from swelled with a hydrocarbon oil or triglyceride oil and commercially available from Shin-Etsu Chemical Co.

The present cosmetic may further comprise one or more of conventional silicone resins. One of the preferred silicone resins is acrylic silicone resin such as acryl/silicone graft copolymer and acryl/silicone block copolymer. The acrylic silicone resin may have at least a residue selected from the group consisting of pyyrolidone residue, long alkyl chain residue, polyoxyalkylene residue, fluoroalkyl residue, and anionic residue such as carboxylic acid residue.

The silicone resin is preferably a network silicone compound, such as MQ resin, MDQ resin, MT resin, MDT resin, and MDTQ resin. Each M, D, T, and Q means $R_3SiO_{0.5}$ unit, $R_2SiO$ unit, $RSiO_{1.5}$ unit, and $siO_2$ unit, respectively, which nomenclature is commonly used in the silicone industry. MT resin and MDT resin are generally known network silicone compounds. The network silicone compound may have MDQ or MDTQ moiety. These silicone resins are commercially available in the form of a solution in octamethylcyclotetrasiloxane. The network silicone compound may have at least a residue selected from the group consisting of pyyrolidone residue, long alkyl chain residue, polyoxyalkylene residue, fluoroalkyl residue and amino residue.

The present cosmetic may comprise one or more of an oil-soluble gelling agent and clay mineral modified with organic compounds.

Examples of the oil-soluble gelling agent include metal soaps such as aluminum stearate, magnesium stearate, and zinc myristate; α-amino acid derivatives such as N-lauroyl-L-glutamic acid, α,γ-di-n-butylamine; dextrin fatty acid esters such as dextrin palmitate, dextrin stearate, and dextrin 2-ethylhexane palmitate; sucrose fatty acid esters such as sucrose palmitate and sucrose stearate; fatty acid esters of fructo-oligosaccharide such as inulinstearate, and 2-ethylhexanoic ester of fructo-oligosaccharide; benzylidene derivatives of sorbitol such as monobenzylidene sorbitol and dibenzylidene sorbitol; clay minerals modified with an organic moiety such as dimethylbenzyldodecylammonium montmorillonite clay, dimethyldioctadecylammonium montmorillonite.

The present cosmetic may comprise one or more of organic UV absorbents. Examples of the organic UV absorbents include UV absorbents of benzoate type, such as p-aminobenzoic acid, ethyl dihydroxypropyl p-aminobenzoate, glyceryl p-aminobenzoate, and octyl p-dimethylaminobenzoate; anthranilic acid type UV absorbents such as methyl anthranilate; UV absorbents of salicylic acid type, such as methyl salicylate, octyl salicylate, and triethanol amine salt of salicylic acid; cinnamic acid type UV absorbents, such as octyl p-methoxycinnamate, diethanol amine salt of p-methoxyhydroxycinnamic acid, and dimethocycinnamic acid/isooctanoic acid gryceride; benzophenone type W absorbents, such as 2,4-dihydroxybenzophenon, 2,2',4,4'-tetrahydroxybenzophenon, 2-hydroxy-4-methyoxybenzophenon, 2-hydroxy-4-methoxypenzophenon-5-sulfonic acid, 2,2'-dihydroxy-4-methoxypenzophenon, and 2-hydroxy-4-N-octoxybenzophenon;

UV absorbents of urocanic acid type, such as ethyl urocanate; UV absorbents of dibenzoylmethane type, such as 4-tert-butyl-4'-methoxydibenzoylmethane, 4-isopropyl dibenzoylmethane; 3-(4-methylbenzylidene) camphor, octyltriazone, e-ethylhexyl-2-cyano-3,3-diphenylacrylate, 2-phenyl-benzoimidasole-5-sulfate, 4-(3,4-dimethoxypnehylmethylene)-2,5-dioxo-1-imidazolidine, and 2-ethylhexylpropionate. The UV absorber may be encapsulated in a polymer powder. The aforesaid powders which absorb or scatter UV ray may be used, for example, titanium oxide fine powder, fine powder of titanium oxide containing iron, zinc oxide fine powder, cerium oxide fine powder and a mixture thereof.

The present cosmetic may further comprise antiseptics or antibacterial agents. Examples of the antiseptics or antibacterial agents include alkyl paraoxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachloromethacresol, hexachlorophene, benzalkonium chloride, chlorohexydine chloride, trichlorocarbanilide, triclosan, photosensitizer, and phenoxyethanol.

Antioxidants may be incorporated in the cosmetic such as tocopherol, butylhydroxyanisole, dibutylhydroxytoluene and phytic acid.

The present cosmetic may further comprise, in an amount not to adversely affect the invention, antiperspirant such as aluminum chlorohydrate, aluminum chloride, aluminum sesquichlorohydrate, zirconyl hydroxy chloride, aluminum zirconium hydroxychloride and aluminum zirconium glycine; pH regulators such as lactic acid, citric acid, glycolic acid, succinic acid, tartaric acid, dl-malic acid, potassium carbonate, sodium hydrogen carbonate and ammonium hydrogen carbonate; chlating agents such as alanine, sodium, sodium polyphosphate, sodium metaphosphate, phosphoric acid; refrigerants such as L-menthol and camphor; and anti-inflammatory agents include allantoin, glycyrrhetinic acid, glycyrrhizinic acid, tranexamic acid, and azulene.

The present cosmetic may further comprises skin-beautifying components in an amount not to adversely affect the invention, such as whitening agents such as placenta extract, arbutin, glutathione and Yukinoshita extract, kojic acid, placenta extract, sulfur, ellagic acid, linoleic acid, tranexamic acid; cell activators, such as royal jelly, photosensitizers, cholesterol derivatives, calf blood extract, α-hydroxy acid and β-hydroxy acid; rough and dry skin improvers; blood circulation improvers, such as nonylic acid vanillyl amide, benzyl nicotinate, β-butoxyethyl nicotinate, capsaicin, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol; and skin colorants such as α-hydroxyacetone.

The present cosmetic may further comprises vitamins in an amount not to adversely affect the invention, e.g. vitamin A such as vitamin A oil, retinol, retinyl acetate and retinyl palmitate; vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin $B_{15}$ and its derivatives; vitamin C, such as L-ascorbic acid, L-ascorbate dipalmitate, sodium (L-ascorbic acid)-2-sulfate and dipotassium L-ascorbic acid diphosphate; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

The present cosmetic may further comprises amino acids such as glycine, valine, leucine, isoleucine, serine, threonine, phenylaranine, alginine, lysine, aspartic acid, glutamic acid, cystine, cysteine, methionine, and tryptophan; examples of the nucleic acids include deoxyribonucleic acid; and examples of the hormones include estradiol and ethenyl estradiol.

The present cosmetic may be in various forms such as liquid, milky lotion, cream, solid, paste, powder, lamella, gel, mousse, stick or spray.

EXAMPLES

The present invention will be further explained in detail below by referring to the examples, though not be limited to these examples. In the examples, "%" means "% by weight" unless otherwise specified.

Triglycerol diallyl ether was prepared by adding ally glycidyl ether dropwise to glycerol in the presence of an alkaline catalyst at 80 degrees C. After the reaction, the catalyst was neutralized and the reaction mixture was subjected to distillation to remove substances with low boiling points. Triglycerol diallyl ether obtained was a pale yellow liquid having a viscosity of 330 mm$^2$/s, a hydroxyl value of 523 KOHmg/g, a unsaturation of 6.13 meq/g, which might be a mixture of the aforesaid isomers of the formula (i) and (ii).

Example 1

Preparation of Alternating Copolymer 1

In a reactor, 200 g of methylhydrogenpolysiloxane represented by the following average compositional formula, 256 g of triglycerol diallyl ether, 400 g of isopropyl alcohol (IPA), and 0.9 g of a 0.5 wt % solution of chloroplatinic acid in IPA were placed and subjected to a reaction for 8 hours while refluxing IPA.

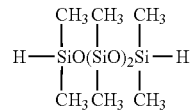

After cooling, the reaction mixture liquid was transferred to an autoclave to which 15 g, weighed in water, of Raney nickel was added. Then, hydrogen gas was introduced in the autoclave and a reaction was carried out at 120 degrees C. for 3 hours while maintaining a pressure of the hydrogen gas at 0.5 MPa. After removing the catalyst by filtration, the reaction mixture was subjected to vacuum distillation to remove volatile substances. The organopolysiloxane/polyglycerol alternating copolymer thus obtained was clear and colorless liquid having a viscosity of 39 Pa·s and a refractive index of 1.4576, both at 25 degrees C.

Example 2

Preparation of Alternating Copolymer 2

In a reactor, 300 g of methylhydrogenpolysiloxane represented by the following average compositional formula, 143 g of triglycerol diallyl ether, 300 g of isopropyl alcohol (IPA), and 0.75 g of a 0.5 wt % solution of chloroplatinic acid in IPA were placed and subjected to a reaction for 8 hours while refluxing IPA.

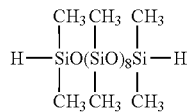

After cooling, the reaction mixture liquid was transferred to an autoclave to which 15 g, weighed in water, of Raney nickel was added. Then, hydrogen gas was introduced in the autoclave and a reaction was carried out at 120 degrees C. for 3 hours while maintaining a pressure of the hydrogen gas at 0.5 MPa.

After removing the catalyst by filtration, the reaction mixture was subjected to vacuum distillation to remove volatile substances. The organopolysiloxane/polyglycerol alternating copolymer thus obtained was clear and colorless liquid having a viscosity of 24 Pa·s and a refractive index of 1.4345, both at 25 degrees C.

Example 3

Preparation of Alternating Copolymer 3

In a reactor, 300 g of methylhydrogenpolysiloxane represented by the following average compositional formula, 67 g of triglycerol diallyether, 300 g of isopropyl alcohol (IPA), and 0.75 g of a 0.5 wt % solution of chloroplatinic acid in IPA were placed and subjected to a reaction for 8 hours while refluxing IPA.

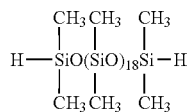

After cooling, the reaction mixture liquid was transferred to an autoclave to which 15 g, weighed in water, of Raney nickel was added. Then, hydrogen gas was introduced in the autoclave and a reaction was carried out at 120 degrees C. for 3 hours while maintaining a pressure of the hydrogen gas at 0.5 MPa.

After removing the catalyst by filtration, a little amount of aldehydes were decomposed with hydrochloric acid. Then, the reaction mixture was neutralized and subjected to vacuum distillation to remove volatile substances. The organopolysiloxane/polyglycerol alternating copolymer thus obtained was clear and colorless liquid having a viscosity of 44 Pa·s and a refractive index of 1.4200, both at 25 degrees C.

Example 4

Preparation of Alternating Copolymer 4

In a reactor, 300 g of methylhydrogenpolysiloxane represented by the following average compositional formula, 28 g of triglycerol diallyl ether, 300 g of isopropyl alcohol (IPA), and 0.75 g of a 0.5 wt % solution of chloroplatinic acid in IPA were placed and subjected to a reaction for 8 hours while refluxing IPA.

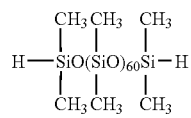

After cooling, the reaction mixture liquid was transferred to an autoclave to which 15 g, weighed in water, of Raney nickel was added. Then, hydrogen gas was introduced in the autoclave and a reaction was carried out at 120 degrees C. for 3 hours while maintaining a pressure of the hydrogen gas at 0.5 MPa.

After removing the catalyst by filtration, a little amount of aldehydes were decomposed by hydrochloric acid. Then, the reaction mixture was neutralized and subjected to vacuum distillation to remove volatile substances. The organopolysiloxane/polyglycerol alternating copolymer thus obtained was clear and colorless liquid having a viscosity of 46 Pa·s and a refractive index of 1.4108, both at 25 degrees C.

Example 5

Preparation of Alternating Copolymer 5

In a reactor, 300 g of methylhydrogenpolysiloxane with a methyl group being replaced with a dodecyl group represented by the following average compositional formula, 29 g of triglycerol diallyl ether, 300 g of isopropyl alcohol (IPA), and 0.75 g of a 0.5 wt % solution of chloroplatinic acid in IPA were placed and subjected to a reaction for 8 hours while refluxing IPA.

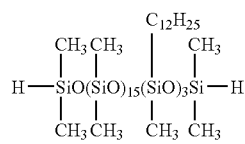

After cooling, the reaction mixture liquid was transferred to an autoclave to which 15 g, weighed in water, of Raney nickel was added. Then, hydrogen gas was introduced in the autoclave and a reaction was carried out at 120 degrees C. for 3 hours while maintaining a pressure of the hydrogen gas at 0.5 MPa.

After removing the catalyst by filtration, a little amount of aldehydes were decomposed by hydrochloric acid. Then, the reaction mixture was neutralized and subjected to vacuum distillation to remove volatile substances. The organopolysiloxane/polyglycerol alternating copolymer thus obtained was clear and pale yellow liquid having a viscosity of 7 Pa·s and a refractive index of 1.4337, both at 25 degrees C.

The alternating copolymer prepared in Example 5 was analyzed with an FT-IR spectrometer SP2000, ex Perkin Elmer, in a thin film coated on a KBr pellet. The presence of OH groups and Si—O—Si bonds in the alternating copolymer were confirmed by strong bands around 3400 cm$^{-1}$ assigned as O—H stretching and 1100-1000 cm$^{-1}$ assigned as Si—O—Si antisymmetric stretching. The presence of methyl groups and Si—C bonds were confirmed by bands around 2960 cm$^{-1}$ assigned as CH$_3$ antisymmetric stretching, 1250 cm$^{-1}$ assigned as CH$_3$ symmetric deformation, and 840 cm$^{-1}$ assigned as Si—C antisymmetric stretching.

Comparative Example 1

Preparation of a Silicone Having Glycerol Residues at Both Terminals

In a reactor, 300 g of methylhydrogenpolysiloxane represented by the following average compositional formula, 122 g of triglycerol diallyether, 300 g of isopropyl alcohol (IPA), and 0.75 g of a 0.5 wt % solution of chloroplatinic acid in IPA were placed and subjected to a reaction for 8 hours while refluxing IPA.

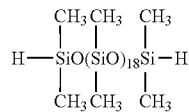

After cooling, the reaction mixture liquid was transferred to an autoclave to which 15 g, weighed in water, of Raney nickel was added. Then, hydrogen gas was introduced in the autoclave and a reaction was carried out at 120 degrees C. for 3 hours while maintaining a pressure of the hydrogen gas at 0.5 MPa.

After removing the catalyst by filtration, a little amount of aldehydes were decomposed by hydrochloric acid. Then, the reaction mixture was neutralized and subjected to vacuum distillation to remove volatile substances. The reaction product, which has a glycerol residue at both terminals, was opaque and pale brown liquid having a viscosity of 69 Pa·s and a refractive index of 1.4285, both at 25 degrees C.

The alternating copolymer 3 and the silicone prepared in Comparative Example 1 were analyzed with GPC using THF as an eluent. A weight average molecular weight of the alternating copolymer 3 was 90,000 and that of the silicone of comparative example 1 was 3,500. Comparing with the silicone having a glycerol residue at both terminals, the present alternating copolymer has an excellent clarity in spite of the higher molecular weight.

Comparative Example 2

Preparation of Silicone Having Glycerol Residues at Both Terminals

In a reactor, 300 g of methylhydrogenpolysiloxane represented by the following average compositional formula, 47 g of triglycerol diallyl ether, 300 g of isopropyl alcohol (IPA), and 0.75 g of a 0.5 wt % solution of chloroplatinic acid in IPA were placed and subjected to a reaction for 8 hours while refluxing IPA.

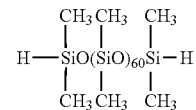

After cooling, the reaction mixture liquid was transferred to an autoclave to which 15 g, weighed in water, of Raney nickel was added. Then, hydrogen gas was introduced in the autoclave and a reaction was carried out at 120 degrees C. for 3 hours while maintaining a pressure of the hydrogen gas at 0.5 MPa.

After removing the catalyst by filtration, a little amount of aldehydes were decomposed by hydrochloric acid. Then, the reaction mixture was neutralized and subjected to vacuum distillation to remove volatile substances. The reaction product, which was a silicone modified with glycerol at both ends, was opaque and pale brown liquid having a viscosity of 233 Pa·s and a refractive index of 1.4150, both at 25 degrees C.

The alternating copolymer 4 and the silicone prepared in Comparative Example 2 were analyzed with GPC using THF as an eluent. A weight average molecular weight of the alternating copolymer 4 was 82,000 and that of the silicone in Comparative Example 2 was 4,500. Comparing with the silicone having a glycerol residue at both terminals, the present alternating copolymer has an excellent clarity in spite of the higher molecular weight.

Example 6. to 8. and Comparative Examples 3, 4

Oily Foundation

Oil-based foundations as seen in the following Table 1 were prepared and evaluated.

TABLE 1

Oil-based Foundation

| Components | Ex*[1]. 6 | Ex. 7 | Ex. 8 | C*[2]. 3 | C. 4 |
|---|---|---|---|---|---|
| 1. Starch fatty acid ester | 6.0 | ← | ← | ← | ← |
| 2. Ceresine | 7.0 | ← | ← | ← | ← |
| 3. Polybutene | 4.0 | ← | ← | ← | ← |
| 4. Liquid paraffin | 34.0 | ← | ← | ← | ← |
| 5. Alternating copolymer 1 | 6.0 | ← | ← | ← | ← |
| 6. Alternating copolymer 2 | | 6.0 | | | |
| 7. Alternating copolymer 4 | | | 6.0 | | |
| 8. Dimetylpolysiloxane (6 cs) | | | | 6.0 | |
| 9. Dimetylpolysiloxane (100 cs) | | | | | 6.0 |
| 10. Titanium oxide | 33.0 | ← | ← | ← | ← |
| 11. Titanated mica | 3.0 | ← | ← | ← | ← |
| 12. Inorganic colored pigment | 7.0 | ← | ← | ← | ← |
| 13. Antiseptic | q.l. | ← | ← | ← | ← |
| 14. Perfume | q.l. | ← | ← | ← | ← |

*[1]: "Ex." means Example.
*[2]: "C" means Comparative Example.

In the table, the numerals represent wt % based on a total weight of the foundation.

Preparation Method

Step 1 Components 1-4 and one of Components 5-9 were dissolved while heating.

Step 2 Components 10-14 were mixed with the resulting mixture from Step 1.

Step 3 The resulting mixture from Step 2 was dispersed homogeneously with a three-roller mill.

Step 4 The resulting mixture from Step 3 was dissolved while heating, degassed, and then poured into a metal plate, followed by cooling.

Evaluation

The foundations were graded by a panel of 50 women in terms of evaluation items shown in table 2 according to the following criteria.

Grading Criteria
Point 5: Excellent
Point 4: good
Point 3: fair
Point 2: poor
Point 1: very poor The averaged grades over the 50 women are as seen in the table 2 where each capital letter means as follows:
A: 4.5 points or higher
B: 3.5 points or higher and lower than 4.5 points
C: 2.5 points or higher and lower than 3.5 points
D: lower than 2.5 points

TABLE 2

| Evaluation Item | Ex. 6 | Ex. 7 | Ex. 8 | C*. 3 | C. 4 |
| --- | --- | --- | --- | --- | --- |
| Product gloss | A | A | A | C | C |
| Spreadability | A | A | A | A | C |
| Affinity | A | A | A | C | B |
| Settleability | A | A | A | D | C |
| Non-tackiness | A | A | A | A | B |
| Moisturized feel | A | A | A | D | C |
| Beautifulness of finish | A | A | A | B | A |
| Durability | A | A | A | D | C |
| Over-all grading | A | A | A | D | C |

As can be seen in Table 2, the foundations of Examples 6 to 8 comprising the present organopolysiloxane/polyglycerol alternating copolymer were superior to those of Comparative Examples 3 and 4 in gloss, spreadability, affinity to skin, settleability, and non-tackiness and gave moisturized and beautiful finish with an excellent durability.

Example 9, 10 and Comparative Examples 5, 6

Lipstick

TABLE 3

| Components | Ex. 9 | Ex. 10 | C. 5 | C. 6 |
| --- | --- | --- | --- | --- |
| 1. Micro crystalline wax | 6.0 | ← | ← | ← |
| 2. Synthetic hydrocarbon wax | 8.0 | ← | ← | ← |
| 3. Cerecine wax | 5.0 | ← | ← | ← |
| 4. Candellila wax | 2.0 | ← | ← | ← |
| 5. Pentaerythritol rosinate | 5.0 | ← | ← | ← |
| 6. Cetyl 2-ethylhexanoate | 20.0 | ← | ← | ← |
| 7. Glyceryl trioctanoate | 25.0 | ← | ← | ← |
| 8. Alternating copolymer 3 | 10.0 | ← | ← | ← |
| 9. Alternating copolymer 5 | | 10.0 | | |
| 10. Methylphenylpolysiloxane | | | 10.0 | |
| 11. Diisostearyl malate | | | | 10.0 |
| 12. Pigment | 5.0 | ← | ← | ← |
| 13. Titanated mica | 15.0 | ← | ← | ← |
| 14. Perfume | q.l. | ← | ← | ← |

In the table, the numerals represent wt % based on a total weight of the lipstick.

Preparation Method

Step 1: All of the components except perfume were dissolved while heating.

Step 2 After degassing the dissolved mixture obtained in Step 1, Component 14 was added and the resulting mixture was poured into a container to form a lipstick.

Evaluation

The lipsticks thus obtained were evaluated in the same manner as in Examples 6 to 8 except that the grading items were those shown in table 4.

TABLE 4

| Evaluation Item | Ex. 9 | Ex. 10 | C. 5 | C. 6 |
| --- | --- | --- | --- | --- |
| Gloss | A | A | A | D |
| Non-tackiness during wearing | A | A | B | D |
| Affinity during wearing | A | A | D | B |
| Non-tackiness after wearing | A | A | B | D |
| Affinity after wearing | A | A | D | B |
| No color transfer | A | A | C | C |
| No color fading | A | A | C | C |
| No color blurring | A | A | D | B |
| Over-all grading | A | A | D | C |

As is evident from Table 4, the lipsticks of Examples 9 and 10 comprising the present organopolysiloxane/polyglycerol alternating copolymer had more shiny gloss of the product surface and had non-tackiness during and after wearing, comparing with the silicones in Comparative Examples 5 and 6. The present invention comprising the present copolymer had an excellent affinity to the lips with no color transferring, color fading, or color blurring.

Example 11

Lipstick

| Components | wt % |
| --- | --- |
| 1. Candelilla wax | 8.0 |
| 2. Polyethylene wax | 8.0 |
| 3. Acrylic silicone resin containing long alkyl chain[1] | 12.0 |
| 4. Metylphenylpolysiloxane[2] | 3.0 |
| 5. Isotridecyl isononanate | 20.0 |
| 6. Glyceryl isostearate | 16.0 |
| 7. Alternating copolymer 2 | 0.5 |
| 8. Octadecyldimethylbenzyl ammonium-modified montmorillonite | 0.5 |
| 9. Polyglyceryl triisostearate | 27.5 |
| 10. Red No. 202 treated with graft copolymer of acrylic - silicone type[3] | 0.8 |
| 11. Iron oxide red treated with graft copolymer of acrylic - silicone type[3] | 1.5 |
| 12. Iron oxide yellow treated with graft copolymer of acrylic - silicone type[3] | 1.0 |
| 13. Iron oxide black treated with graft copolymer of acrylic - silicone type[3] | 0.2 |
| 14. Titanium oxide treated with graft copolymer of acrylic - silicone type[3] | 1.0 |
| 15. Antiseptic | q.l. |
| 16. Perfume | q.l. |

[1] Acrylic silicone resin containing long alkyl chain: KP-561P (from Shin-Etsu Co., Ltd.)
[2] Metylphenylpolysiloxane: KF-54 (from Shin-Etsu Co., Ltd.)
[3] Acrylic - silicone type graft copolymer: KP-541 (from Shin-Etsu Co., Ltd.)

(Preparation)

Step 1 Components 1-8 and a portion of Component 9 were mixed while heating to dissolve.

Step 2 Components 10-16 and the rest of Component 9 were mixed homogeneously, and then the resulting mixture was added to the mixture from Step 1 to obtain a homogeneous mixture.

The lipstick thus obtained had a shiny gloss on its surface, extended lightly, had a non-tacky and non-powdery touch, and left to the lips refreshed and lightweight feel. The applied lipstick had good water resistance, water repellency and was durable and stable.

Example 12

Brushing Spray

| Components | wt % |
| --- | --- |
| 1. Isopropyl myristate | 0.8 |
| 2. Stearyltrimethylammonium chloride | 0.05 |
| 3. Alternating copolymer 1 | 0.5 |
| 4. Aluminum magnesium silicate | 0.1 |
| 5. Zinc oxide treated with oil | 3.0 |
| 6. Ethanol | 25.0 |
| 7. Perfume | q.l. |
| 8. Propellent | Balance |

(Preparation Method)

Step 1 Components 1-7 were mixed.

Step 2 The resulting mixture from Step 1 was put in an aerosol can, to which Component 8 was put to obtain a brushing agent.

The brushing spray thus obtained gave a shiny and smooth finish. It also demonstrated a good dispersibility of powder during application and made hair shiny and easy to comb.

Example 13

Roll-on Antiperspirant

| Components | wt % |
| --- | --- |
| 1. Crosslinked polyether-modified silicone[1] | 20.0 |
| 2. Dimethylpolysiloxane (6 mm²/sec at 25 degrees C.) | 10.0 |
| 3. Crosslinked dimethylpolysiloxane[2] | 14.3 |
| 4. Decamethylcyclopentasiloxane | 30.0 |
| 5. Alternating copolymer 4 | 0.5 |
| 6. Organo-modified Bentonite | 0.2 |
| 7. Aluminum Zirconium Tetrachlorohydrate | 20.0 |
| 8. Zinc oxide treated with dimethylmethylhydrogen | 5.0 |
| 9. Perfume | q.l. |

[1]Crosslinked polyether-modified silicone: KSG-210 (from Shin-Etsu Co., Ltd)
[2]Crosslinked dimethylpolysiloxane: KSG-15 (from Shin-Etsu Co., Ltd.)

(Preparation Method)

Step 1 Components 1-6 were mixed.

Step 2 To the resulting mixture from Step 1, Components 7-9 were added to disperse homogeneously.

The roll-on antiperspirant spread lightly on the skin, gave a refreshed feeling, and had a non-tacky and non-greasy touch. It did not show quality change with temperature change and with time, showing good properties for use and stability.

Example 14

Cleansing Composition

| Components | wt % |
| --- | --- |
| 1. POE (10) Sorbitan monolaureate[1] | 30.0 |
| 2. Sodium chloride | 1.0 |
| 3. Purified water | 49.0 |
| 4. Alternating copolymer 1 | 20.0 |

[1]Polyoxyethylene (10) sorbitan monolaureate, ex Sanyo Kasei Co.

Preparation Method

Components 1-4 were mixed.

The cleansing composition thus obtained was clear and had good compatibility with lipstick and/or foundation to show high cleansing effect. It spread well in use. After use, the skin was moisturized and non-tacky.

Example 15

Makeup Remover

| Components | wt % |
| --- | --- |
| 1. POE (6) Sorbitan Monolaureate[1] | 5.0 |
| 2. Alternating copolymer 1 | 5.0 |
| 3. Alternating copolymer 2 | 15.0 |
| 4. Ethanol | 10.0 |
| 5. Glycerin | 2.0 |
| 6. Dipropylene Glycol | 3.0 |
| 7. Sodium Glutamate | 0.5 |
| 8. Antiseptic | q.l. |
| 9. Perfume | q.l. |
| 10. Purified water | 59.5 |

[1]POE (6) Sorbitan Monolaureate, ex Sanyo Kasei Co.

(Preparation Method)

Step 1: Components 1-8 and 10 were combined and dissolved homogeneously.

Step 2: To the resulting mixture from Step 1, Component 9 was added to obtain a makeup remover.

Upon using the makeup remover thus obtained, the makeup remover was found to be compatible with cosmetics and sebum and have good cleansing effect. It spread well in use. After use, the skin was moisturized and non-tacky.

Example 16

Polyalcohol-in-Oil Emulsified Cosmetic

| Components | wt % |
| --- | --- |
| 1. Crosslinked dimethylpolysiloxane[1] | 30.0 |
| 2. decamethylcyclopentasiloxane | 15.0 |
| 3. Dimethylpolysiloxane (6 mm²/sec at 25 degrees C.) | 7.0 |
| 4. Alternating copolymer 3 | 3.0 |
| 5. Dimethyldistearylammonium hectorite | 2.0 |

| Components | wt % |
| --- | --- |
| 6. Antiseptic | q.l. |
| 7. Perfume | q.l. |
| 8. Sodium chloride | 0.05 |
| 9. 1,3-butylene glycol | 42.95 |

[1])Crosslinked dimethylpolysiloxane: KSG15 (from Shin-Etsu Chemical Industries Co., Ltd.)

(Preparation Method)
Step 1: Components 1-5 and 7 were mixed homogeneously.
Step 2: Components 6, 8, and 9 were mixed.
Step 3: The resulting mixture from Step 2 was added to the resulting mixture from Step 1 to emulsify homogeneously.

The polyalcohol-in-oil emulsified cosmetic thus obtained was stable, spread lightly on the skin and had a non-tacky and non-greasy touch. After use, the skin was moisturized.

Example 17

Solid Emulsified Blush of Polyalcohol-in-Oil Type

| Components | wt % |
| --- | --- |
| 1. Crosslinked dimethylpolysiloxane[1]) | 5.0 |
| 2. Decamethylcyclopentasiloxane | 5.0 |
| 3. Dimethylpolysiloxane (6 mm$^2$/sec at 25 degrees C.) | 19.7 |
| 4. Cetyl Isooctanoate | 15.0 |
| 5. Paraffin wax (mp; 80 degrees C.) | 12.0 |
| 6. Alternating copolymer 3 | 3.0 |
| 7. Dimethyldisearylammonium hectorite | 0.2 |
| 8. Powder treated for hydrophobicity | 25.0 |
| 9. Antiseptic | q.l. |
| 10. Perfume | q.l. |
| 11. 1,3-Dibutylene glycol | 15.0 |

[1])Crosslinked dimethylpolysiloxane: KSG15 (from Shin-Etsu Chemical Co., Ltd.)

(Preparation Method)
Step 1: Components 1-7 and 11 were heated to 80 degrees C. to mix homogeneously.
Step 2: Component 8 was added to the resulting mixture from Step 1 and dispersed homogeneously.
Step 3: Components 9, 10, and 12 were heated to 80 degrees C. and the resulting mixture was added to the mixture from Step 2 to pour into a metal plate to cool down.

The solid emulsified blush of polyalcohol-in-oil was stable, spread lightly on the skin, and had a non-tacky and non-greasy touch. After use, the skin was moisturized.

Example 18

Creamy Lipstick

| Components | wt % |
| --- | --- |
| 1. Palmitic acid/dextrin ethylhexanoate[1]) | 9.0 |
| 2. Glyceryl triisooctanoate | 22.0 |
| 3. Bentonite | 0.7 |
| 4. Alternating copolymer 4 | 1.5 |
| 5. M3T-C6 | 42.0 |
| 6. 1,3-butylene glycol | 5.0 |
| 7. Sodium chloride | 0.5 |
| 8. Purified water | 19.3 |
| 9. Coloring pigment | q.l. |

[1])Palmitic acid/dextrin ethylhexanoate: Rheopal TT (from Chiba Seifun Co., Ltd.)

(Preparation Method)
Step 1: Portions of Components 1 and 2 and Components 3-5 were mixed to dissolve.
Step 2: To the rest of Component 2, Component 9 was added to disperse with rollers.
Step 3: To the resulting mixture from Step 2, the mixture from Step 1 was added and mixed homogeneously.
Step 4: Components 6-8 were mixed while heating.
Step 5: The resulting mixture from Step 4 was added to the mixture from Step 3 to emulsify.

The lipstick thus obtained was a long wearing creamy lipstick of w/O type, spread lightly, and had a non-tacky and non-greasy touch.

Example 19

Eye Liner

| Components | wt % |
| --- | --- |
| 1. Octamethylcyclotetrasiloxane | 53.5 |
| 2. Alternating copolymer 4 | 3.0 |
| 3. Network silicone resin[1]) | 15.0 |
| 4. Dimethylstearyammonium hectolite | 3.0 |
| 5. Silicone-treated iron oxide black[2]) | 10.0 |
| 6. 1,3-butylene glycol | 5.0 |
| 7. Sodium sulfate | 0.5 |
| 8. Antiseptic | q.l. |
| 9. Perfume | q.l. |
| 10. Purified water | 10.0 |

[1])Network silicone resin: KF7312J (from Shin-Etsu Chemical Co., Ltd.): a 50% solution in D5 of a network silicone compound having a ratio, $[Me_3SiO_{1/2}]/[SiO_2]$, of 0.8.
[2])Silicone-treated Iron oxide black: 2% of methylhydrogen-polysiloxane was added to iron oxide black, followed by a heat treatment.

(Preparation Method)
Step 1: Components 1-4 were mixed while heating, and Component 5 was added to disperse homogeneously.
Step 2: Components 6-9 were mixed.
Step 3: While stirring, the resulting mixture from Step 2 was added portionwise to the resulting mixture from Step 1 to obtain an eye liner.

The eye liner thus obtained spread lightly on the skin, was easy to draw, gave a refreshed and non-tacky feeling. It did not show quality change with temperature change or with time, showing superior properties for use and stability. It had good water resistance as well as sweat resistance and the makeup coverage lasted long.

Example 20

Eye Shadow

| Components | wt % |
|---|---|
| 1. Decametylpentasiloxane | 15.0 |
| 2. Dimethylpolysiloxane | 10.0 |
| 3. Alternating copolymer 4 | 2.0 |
| 4. PEG(10) laurylether | 0.5 |
| 5. Silicone-treated chromium oxide[1] | 6.2 |
| 6. Silicone-treated ultramarine blue[1] | 4.0 |
| 7. Silicone-treated titanium-coated mica[1] | 6.0 |
| 8. Sodium chloride | 2.0 |
| 9. Propylene glycol | 8.0 |
| 10. Antiseptic | q.l. |
| 11. Perfume | q.l. |
| 12. Purified water | 46.3 |

[1]Silicone treatment: 3%, based on the powder, of methylhydrogenpolysiloxane was added to the powder, followed by heat treatment.

(Preparation Method)

Step 1: Components 1-4 were mixed, and Component 5-7 were added to disperse homogeneously.

Step 2: Components 8-10 and Component 12 were dissolved homogeneously.

Step 3: While stirring, the resulting mixture from Step 2 was added portionwise to the resulting mixture from Step 1 to emulsify, to which Component 11 was added to obtain an eye shadow.

The eye shadow thus obtained spread lightly on the skin, was non-greasy and non-powdery. It gave a moisturized and refreshed feeling to the users. It also had good water resistance, water repellency and good sweat resistance. The coverage lasted long. It did not show quality change with temperature change or with time, showing superior stability.

Example 21

Suntan Milky Lotion

| Components | wt % |
|---|---|
| 1. Emulsifier composition[1] | 6.0 |
| 2. Dimethylpolysiloxane (6 mm$^2$/sec at 25 degrees C.) | 49.0 |
| 3. 1,3-butylene glycol | 5.0 |
| 4. Sodium dehydroacetate | 0.2 |
| 5. Antioxidant | q.l. |
| 6. Antiseptic | q.l. |
| 7. Perfume | q.l. |
| 8. Purified water | 39.8 |

[1]The emulsifier composition contained: a. Alternating copolymer 4 10 parts by weight, b. Dioctadecyldimethylammonium-modified montmorillonite: 10.0 parts by weight, and c. Ethanol: 40.0 parts by weight.

(Preparation Method)

Step 1 Component a was dissolved in Component c and Component b was added.

Step 2 The resulting mixture from Step 1 was stirred for an hour with a disperser and then ethanol was evaporated with a evaporator.

Step 3 The resulting mixture from Step 2 was dried overnight at 50 degrees C. to obtain an emulsified composition, Component 1.

Step 4 Component 1, obtained in Step 3, was mixed with Component 2.

Step 5 Components 3-6 and 8 were mixed homogeneously.

Step 6 Under stirring, the resulting mixture from Step 4 was added portionwise to the resulting mixture from Step 5 to emulsify and then Component 7 was added to obtain a suntan milky lotion.

The suntan milky lotion thus obtained spread lightly on the skin, had a fine texture and a non-tacky and non-greasy touch, left skin moisturized, hydrated and refreshed feeling to the users, was water-proof and the coverage wore long. It did not also show quality change with temperature change or with time, showing superior stability.

Example 22

Suncut Cream

| Components | wt % |
|---|---|
| 1. Decamethylcyclepentasiloxane | 17.5 |
| 2. Acrylic silicone resin/decamethylcyclopentasiloxane[1] | 12.0 |
| 3. Glyceryl triisooctanoate | 5.0 |
| 4. Octyl para-methoxycinnamate | 6.0 |
| 5. Cross-linked polyether-modified silicone[2] | 5.0 |
| 6. Alternating copolymer 5 | 1.0 |
| 7. Zinc oxide treated for lipophilicity | 20.0 |
| 8. Sodium chloride | 0.5 |
| 9. 1,3-butylene glycol | 2.0 |
| 10. Antiseptic | q.l. |
| 11. Perfume | q.l. |
| 12. Purified water | 31.0 |

[1]Acrylic silicone/decamethylcyclopentasiloxane: KP545 (from Shin-Etsu Co., Ltd.)
[2]Cross-linked polyether-modified silicone: KSG21 (from Shin-Etsu Co., Ltd.)

(Preparation Method)

Step 1: To a portion of Component 1, Component 2 was added and mixed homogeneously, to which Component 7 was added and dispersed with a beads mill.

Step 2: The rest of Component 1 and Components 3-6 were combined to mix homogeneously.

Step 3: Component 8-10 and 12 were mixed to dissolve homogeneously.

Step 4: To the resulting mixture from Step 2, the mixture from Step 3 was added and emulsified, to which the mixture from Step 1 and Component 11 were added to obtain a suncut cream.

The suncut cream thus obtained spread lightly on the skin, had a non-tacky touch, demonstrated good affinity with skin, clung tightly to the skin, and gave a shiny finish. It also exhibited a long lasting coverage and no quality change was observed with temperature change or with time.

Example 23

Suntan Cream

| Components | wt % |
|---|---|
| 1. Decamethylcyclepentasiloxane | 15.0 |
| 2. Dimethylpolysiloxane (6 mm$^2$/sec at 25 degrees C.) | 5.0 |
| 3. Stearyl-modified acrylic silicone[1] | 0.5 |
| 4. Alternating copolymer 4 | 6.0 |

-continued

| Components | wt % |
| --- | --- |
| 5. Palmitic acid | 0.2 |
| 6. Dimethyloctyl paraaminobenzoic acid | 0.5 |
| 7. Kaoline | 0.5 |
| 8. Iron oxide red | 0.2 |
| 9. Iron oxide yellow | 0.3 |
| 10. Iron oxide black | 0.1 |
| 11. Titanium oxide coated mica | 1.0 |
| 12. Sodium L-glutamate | 3.0 |
| 13. 1,3-butylene glycol | 5.0 |
| 14. Dioctadecyldimethyl ammonium chloride | 0.1 |
| 15. Antioxidant | q.l. |
| 16. Antiseptic | q.l. |
| 17. Perfume | q.l. |
| 18. Purified water | 62.1 |

[1] Stearyl-modified acrylic silicone: KP-561P (from Shin-Etsu Chemical Co., Ltd.)

(Preparation Method)

Step 1: Components 1-7 and Components 16-17 were dissolved while heating.

Step 2: After stirring Component 15 and a portion of Component 19 while heating, Components 8-12 were added to disperse.

Step 3: Components 13-14 and the remaining portion of Component 19 were dissolved homogeneously and combined with the resulting mixture from Step 2.

Step 4: While stirring, the resulting mixture from Step 3 was added portionwise to the resulting mixture from Step 1 to emulsify and cooled, to which Component 18 was added to obtain a suntan cream.

The suntan cream thus obtained spread lightly on the skin, had a fine texture and a non-tacky and non-greasy touch, and provided moisturized, hydrated and refreshed feeling to the users. It also clung tightly to the skin and gave a long lasting coverage. It did not show quality change with temperature change or with time, such as separation or flocculation of the power, showing good stability.

Example 24

Suncut Milky Lotion

| Components | wt % |
| --- | --- |
| 1. Decamethylcyclopentasiloxane | 3.0 |
| 2. Dimethylpolysiloxane with a viscosity of 6 mm$^2$/sec | 5.0 |
| 3. Glyceryl triisooctanoate | 5.0 |
| 4. Alternating copolymer 3 | 1.0 |
| 5. Crosslinked polyether-modified silicone[1] | 3.0 |
| 6. Titanium oxide/decamethylcyclopentasiloxane dispersion[2] | 25.0 |
| 7. Zinc oxide/decamethylcyclopentasiloxane dispersion[3] | 35.0 |
| 8. Dipropyleneglycol | 3.0 |
| 9. Sodium citrate | 0.5 |
| 10. Antiseptic | q.l. |
| 11. Perfume | q.l. |
| 12. Purified water | 19.5 |

[1] Crosslinked polyether-modified silicone: KSG-21 (from Shin-Etsu Co., Ltd.)
[2] Titanium oxide/decamethylcyclopentasiloxane dispersion: SPD-T1S (from Shin-Etsu Co., Ltd.)
[3] Zinc oxide/decamethylcyclopentasiloxane dispersion: SPD-Z5 (from Shin-Etsu Co., Ltd.)

(Preparation Method)

Step 1 Components 1-5 were combined to mix homogeneously.

Step 2 Components 8, 10 and 12 were combined to dissolve.

Step 3 To the resulting mixture from Step 1, the mixture from Step 2 was added, and then Component 6, 7 and 11 were added to obtain a suncut milky lotion.

The suncut milky lotion spread lightly on the skin, had a non-tacky touch, exhibited a good affinity with skin, clung tightly to the skin, and gave a shiny finish. The coverage lasted long and no quality change was observed with temperature change or with time.

Example 25

Foundation

| Components | wt % |
| --- | --- |
| 1. Decamethylcyclopentasiloxane | 45.0 |
| 2. Dimethylpolysiloxane with a viscosity of 6 mm$^2$/sec | 5.0 |
| 3. Alternating copolymer 2 | 1.5 |
| 4. Alternating copolymer 4 | 0.5 |
| 5. Hectorite modified with dimethyldistearylammonium salt | 4.0 |
| 6. Titanium dioxide treated for hydrophobicity[1] | 10.0 |
| 7. Talc treated for hydrophobicity[1] | 6.0 |
| 8. Mica treated for hydrophobicity[1] | 6.0 |
| 9. Iron oxide red treated for hydrophobicity[1] | 1.6 |
| 10. Iron oxide yellow treated for hydrophobicity[1] | 0.7 |
| 11. Iron oxide black treated for hydrophobicity[1] | 0.2 |
| 12. Dipropylene glycol | 5.0 |
| 13. Methyl paraoxybenzoate | 0.3 |
| 14. 2-amino-2-methyl-1,3-propanediol | 0.2 |
| 15. Hydrochloric acid | 0.1 |
| 16. Perfume | q.l. |
| 17. Water | 13.9 |

[1] Treatment for hydrophobicity: after adding 2% of KF-9909 to the powder, a heat treatment was applied.

(Preparation Method)

Step 1: Components 1-5 were mixed while heating and Components 6-11 were added to obtain a homogeneous mixture.

Step 2: Components 12-15 and Component 17 were dissolved while heating (pH of the aqueous system: 9.0).

Step 3: While stirring, the resulting mixture from Step 2 was added portionwise to the resulting mixture from Step 1 to emulsify and cooled, to which Component 16 was added to obtain foundation.

The foundation thus obtained spread lightly on the skin, had a fine texture and a non-tacky and non-greasy touch, and provided moisturized, hydrated and refreshed feeling to the users. The makeup coverage lasted long and it did not show quality change with temperature change or with time, showing good stability.

Example 26

Liquid Foundation

| Components | wt % |
| --- | --- |
| 1. Decamethylcyclopentasiloxane | 16.0 |
| 2. Dimethylpolysiloxane with a viscosity of 6 mm$^2$/sec | 8.0 |
| 3. Octyl paramethoxycinnamate | 3.0 |
| 4. 12-hydroxysteatic acid | 1.0 |
| 5. Alternating copolymer 5 | 2.0 |
| 6. Fluorinated silicone[1] | 5.0 |
| 7. Spherical silicone resin powder[2] | 3.0 |

-continued

| Components | wt % |
| --- | --- |
| 8. Fine particle titanium oxide treated with a fluorine compound[3] | 8.0 |
| 9. Mica titanium treated with a fluorine compound[3] | 1.0 |
| 10. Titanium oxide treated with a fluorine compound[3] | 5.0 |
| 11. Iron oxide red treated with a fluorine compound[3] | 0.9 |
| 12. Iron oxide yellow treated with a fluorine compound[3] | 2.0 |
| 13. Iron oxide black treated with a fluorine compound[3] | 1.0 |
| 14. Ethanol | 15.0 |
| 15. Glycerin | 3.0 |
| 16. Magnesium sulfate | 1.0 |
| 17. Antiseptic | q.l. |
| 18. Perfume | q.l. |
| 19. Purified water | 25.1 |

[1] Fluorinated silicone: FL-5 (from Shin-Etsu Chemical Co., Ltd.)
[2] Spherical silicone resin powder: KMP-590 (from Shin-Etsu Chemical Co., Ltd.)
[3] Treatment with a fluorine compound: coated with 5% of perfluoroalkylethylphosphate diethanolamine salt (Preparation Method)
Step 1: Components 7-13 were mixed homogeneously.
Step 2: Components 1-6 were mixed while heating to 70 degrees C., to which the resulting mixture from Step 1 was added to obtain a homogeneous dispersion.
Step 3. Components 14-17 and Component 19 were heated to 40 degrees C. and added portionwise to the resulting mixture from Step 2 to emulsify and cooled, to which Component 18 was added to obtain a liquid foundation.

The foundation thus obtained spread lightly on the skin, was non-tacky, and gave a refreshed feeling to the users. It did not show quality change with temperature change or with time, showing superior stability.

Example 27

Hair Cream

| Components | wt % |
| --- | --- |
| 1. Decamethylcyclopentasiloxane | 10.0 |
| 2. Methyphenylpolysiloxane | 5.0 |
| 3. Squalane | 4.0 |
| 4. Network silicone resin[1] | 1.0 |
| 5. Glyceryl dioleate | 2.0 |
| 6. Alternating copolymer 4 | 4.0 |
| 7. Sodium sorbitol sulfate | 2.0 |
| 8. Sodium chondroitin sulfate | 1.0 |
| 9. Sodium hyaluronate | 0.5 |
| 10. Propylene glycol | 3.0 |
| 11. Antiseptic | 1.5 |
| 12. Vitamin E acetate | 0.1 |
| 13. Antioxidant | q.l. |
| 14. Perfume | q.l. |
| 15. Purified water | 65.9 |

[1] Network silicone resin: 50% solution in D5 of network silicone compound with a [Me$_3$SiO$_{1/2}$]/[SiO$_2$] ratio of 0.8:KF7312J (from Shin-Etsu Chemical Co., Ltd.)

(Preparation Method)
Step 1: Components 1-6 and Components 11-13 were mixed while heating.
Step 2: Components 7-10 and Component 15 were mixed to dissolve.
Step 3: While stirring, the resulting mixture from Step 2 was added portionwise to the resulting mixture from Step 1 to emulsify and after cooled, Component 15 was added to obtain a hair cream.

The hair cream thus obtained spread lightly on the skin, demonstrated a non-tacky and non-greasy touch and gave hair a moisturized and refreshed feeling. It also had good water resistance and repellency, and good sweat resistance and the coverage lasted long. It showed no quality change with temperature change or with time, showing good stability.

Example 28

Hair Cream

| Components | wt % |
| --- | --- |
| 1. Dissolved silicone gum (400,000 mPa sec) | 18.0 |
| 2. Silicone network resin[1] | 6.0 |
| 3. Glyceryl tri-2-ethylhexenoic acid | 8.0 |
| 4. Vaseline | 5.0 |
| 5. Stearyl alcohol | 2.0 |
| 6. Sorbitan monoleaate | 2.0 |
| 7. Alternating copolymer 4 | 2.0 |
| 8. Glycerol | 5.0 |
| 9. Sodium chloride | 0.5 |
| 10. Perfume | q.l. |
| 11. Purified water | 51.5 |

[1] A 50% solution of network silicone compound in D5 with a ratio of [Me$_3$SiO$_{1/2}$]/[SiO$_2$] of 0.8:KF7312J (from Shin-Etsu Chemical Co., Ltd.)

(Preparation Method)
Step 1 Components 1-7 were mixed while heating.
Step 2 Components 8-9 and 11 were mixed and stirred.
Step 3 While stirring, to the resulting mixture from Step 2, the resulting mixture from Step 1 was added portionwise to emulsify, to which Component 10 was added to obtain a hair cream.

The hair cream thus obtained spread lightly on the skin, had a non-tacky and non-greasy touch, left moisturized, hydrated, and refreshed feeling, and gave hair shiny gloss and smoothness. It was also found that it had a good setting effect for hair.

Example 29

Moisturizing Cream

| Components | wt % |
| --- | --- |
| 1. Decamethylcyclopentasiloxane | 10.0 |
| 2. Methylphenylpolysiloxane | 3.0 |
| 3. Liquid paraffin | 5.0 |
| 4. Stearoxy-modified silicone[1] | 8.0 |
| 5. Alternating copolymer 4 | 2.0 |
| 6. Spherical organopolysilxane elastomer powder[2] | 2.5 |
| 7. Silica treated for hydrophobicity[3] | 2.0 |
| 8. Zinc Stearate | 2.0 |
| 9. Vitamin E acetate | 3.0 |
| 10. Polyethylene glycol 400 | 1.0 |
| 11. Sodium lactate | 1.0 |
| 12. 1,3-butylene glycol | 5.0 |
| 13. Antiseptic | q.l. |
| 14. Perfume | q.l. |
| 15. Purified water | 55.5 |

[1] Stearoxy-modified silicone: KF-7002 (from Shin-Etsu Co., Ltd.)
[2] Spherical organopolysilxane elastomer powder: KMP-590 (from Shin-Etsu Co., Ltd.)
[3] Silica treated for hydrophobicity: Aerosil R972 (from Nippon Aerosil Corp.)

(Preparation Method)
Step 1 Components 1-5, 8, and 9 were mixed homogeneously, to which the Components 6-7 were added and dispersed homogeneously.

Step 2 Components 10-13 and 15 were combined to dissolve.

Step 3 The resulting mixture from Step 2 was added portionwise to that from Step 1 and cooled, to which Component 14 was added to obtain a moisturizing cream.

The moisturizing cream thus obtained spread lightly on the skin, had a non-tacky touch and gave skin moisturized and hydrated feel. It did not show quality change with temperature change or with time, showing good stability.

Example 30

Hand Cream

| Components | % |
| --- | --- |
| 1. Decamethylcyclepentasiloxane | 30.0 |
| 2. Liquid paraffin | 10.0 |
| 3. Gummy amino-modified silicone (amine equivalent weight; 70000 g/mol) | 15.0 |
| 4. Alternating copolymer 3 | 4.0 |
| 5. Distearyldimethyl ammonium chloride | 0.8 |
| 6. Vitamin E acetate | 0.1 |
| 7. Polyethylene glycol 4000 | 1.0 |
| 8. Glycerin | 10.0 |
| 9. Aluminum magnesium silicate | 1.2 |
| 10. Antiseptic | q.l. |
| 11. Perfume | q.l. |
| 12. Purified water | 27.9 |

(Preparation Method)

Step 1: Components 1 and 3 were mixed to dissolve while heating, and Components 2, 4-6 and 10 were added while heating.

Step 2: Components 7-9 and Component 12 were mixed under heating.

Step 3: The resulting mixture from Step 2 was added portionwise to the resulting mixture from Step 1 to emulsify and cooled, to which Component 11 was added to obtain a hand cream.

The hand cream thus obtained spread lightly on the skin, was non-sticky, and gave the users a refreshing feel. It protected skin when working with water and did not show quality change with temperature change or with time, showing superior stability.

Example 31

O/W Cream

| Components | wt % |
| --- | --- |
| 1. Acrylic silicone resin/decamethylpentasiloxane[1] | 10.0 |
| 2. Stearyl-modified acrylic silicone[2] | 8.0 |
| 3. Cetanol | 1.0 |
| 4. Glyceryl triisostearate | 5.0 |
| 5. Stearic acid | 3.0 |
| 6. Glyceryl monostearate | 1.5 |
| 7. Alternating copolymer 2 | 0.7 |
| 8. Sorbitan sesquioleate | 0.5 |
| 9. Polyoxyethylene sorbitan monooleate | 1.0 |
| 10. Sodium hydroxide (1% aqueous solution) | 10.0 |
| 11. 1,3-butylene glycol | 5.0 |
| 12. Antiseptic | q.l. |
| 13. Perfume | q.l. |
| 14. Purified water | 54.3 |

[1]Acrylic silicone resin/decamethylpentasiloxane: KP-545 (from Shin-Etsu Chemical Co., Ltd.)
[2]Stearyl-modified acrylic silicone: KP-561P (from Shin-Etsu Chemical Co., Ltd.)

(Preparation Method)

Step 1: Components 1-9 were mixed and dissolved while heating.

Step 2: Components 10-12 and Component 14 were mixed and heated.

Step 3: The resulting mixture from Step 2 was added to the resulting mixture from Step 1 to emulsify, to which Component 13 was added to obtain an O/W hand cream.

The O/W cream thus obtained was non-tacky, spread lightly on the skin, had a high affinity with skin, clung tightly to the skin, and gave a shiny finish. It provided a long lasting cosmetic coverage and superior stability and did not show quality change with temperature change or with time.

Example 32

Milky Lotion

| Components | wt % |
| --- | --- |
| 1. Decamethylcyclopentasiloxane | 15.0 |
| 2. Mehtylphenylpolysiloxane | 5.0 |
| 3. Squalene | 5.0 |
| 4. Pentaerythritol tetra-2-ethylhexanoate | 5.0 |
| 5. Alternating copolymer 4 | 3.0 |
| 6. Spherical organopolysilxane elastomer powder[1] | 2.0 |
| 7. Hydrophobic silica[2] | 0.5 |
| 8. Magnesium ascorbate | 1.0 |
| 9. Sodium chloride | 1.0 |
| 10. Polyethylene glycol 11000 | 1.0 |
| 11. Propylene glycol | 8.0 |
| 12. Antiseptic | q.l. |
| 13. Perfume | q.l. |
| 14. Purified water | 53.5 |

[1]Spherical organopolysilxane elastomer powder: KMP-590 (from Shin-Etsu Chemical Co., Ltd.)
[2]Hydrophobic silica: Aerosil R972 (from Nippon Aerosil Corp.): Hydrophobic silica (Preparation Method)

Step 1: Components 1-5 were mixed homogeneously and Components 6-7 were added to disperse homogeneously.

Step 2: Components 8-10 were added to Component 14 to dissolve, to which a homogeneous mixture of Components 11 and 12, was added.

Step 3: The resulting mixture from Step 2 was added portionwise to the resulting mixture from Step 1 to emulsify and cooled, to which Component 13 was added to obtain a milky lotion.

The milky lotion thus obtained spread lightly on the skin, was light and non-tacky, and did not show quality change with temperature change or with time, showing superior stability and properties for use.

Example 33

Beautifying Liquid

| Components | wt % |
| --- | --- |
| 1. Decamethylcyclopentasiloxane | 12.0 |
| 2. Glyceryl triisooctanoate | 10.0 |
| 3. Alternating copolymer 4 | 2.0 |
| 4. Alternating copolymer 5 | 0.2 |
| 5. Glycerin | 10.0 |

-continued

| Components | wt % |
|---|---|
| 6. Magnesium ascorbate phosphate | 3.0 |
| 7. Sodium chloride | 2.0 |
| 8. Antiseptic | q.l. |
| 9. Perfume | q.l. |
| 10. Purified water | 60.8 |

(Preparation Method)
Step 1: Components 1-4 were mixed while.
Step 2: Components 5-8 and Components 10 were heated to dissolve homogeneously.
Step 3: While stirring the resulting mixture from Step 2 was added portionwise to the resulting mixture from Step 1 to emulsify to obtain a beautifying liquid.

The beautifying liquid thus obtained spread lightly on the skin, had a fine texture and a non-tacky touch, and provided moisturized and non-tacky feel to users. It did not show quality change with temperature change or with time, showing good stability.

Example 34

Antiperspirant

| Components | wt % |
|---|---|
| 1. Octamethylcyclopentasiloxane | 30.0 |
| 2. Alternating copolymer 4 | 1.0 |
| 3. Polyoxyethylenesorbitan monooleate (20 E.O.) | 0.5 |
| 4. Aluminum zirconium tetrachlorohydrate glycine salt | 20.0 |
| 5. Purified water | 48.5 |

(Preparation Method)
Step 1: Components 1 and 2 were mixed.
Step 2: Component 4 was dissolved in Component 5, to which Component 3 was added.
Step 3: While stirring, the resulting mixture from Step 2 was added portionwise to the resulting mixture from Step 1 to emulsify to obtain an antiperspirant.

The antiperspirant thus obtained could be extended lightly on the skin, had a non-tacky and non-greasy touch, did not leave too much white powdery residue, and gave a refreshed feeling to the users. It did not show quality change with temperature change or with time, showing superior stability.

Example 35

Cleansing Cream

| Components | wt % |
|---|---|
| 1. Dimethylpolysiloxane with a viscosity of 6 mm²/sec | 5.0 |
| 2. Methylphenylpolysiloxane | 5.0 |
| 3. Liquid paraffin | 8.0 |
| 4. Jojoba oil | 2.0 |
| 5. Alternating copolymer 4 | 2.5 |
| 6. Alternating copolymer 5 | 0.5 |
| 7. Dextrin fatty acid ester | 0.8 |
| 8. Aluminum monostearate | 0.2 |

-continued

| Components | wt % |
|---|---|
| 9. Aluminum chloride | 1.0 |
| 10. Glycerin | 10.0 |
| 11. Antiseptic | q.l. |
| 12. Perfume | q.l. |
| 13. Purified water | 65.0 |

(Preparation Method)
Step 1 Components 1-8 were blended while heating.
Step 2 Components 9-11 and 13 were dissolved while heating.
Step 3 While stirring, the resulting mixture from the Step 2 was added portionwise to that from Step 1 and cooled, to which Component 12 was added to obtain a cleansing cream.

The cleansing cream thus obtained spread lightly on the skin, had a fine texture and a non-tacky and non-greasy touch, and left skin moisturized, hydrated and refreshed feeling. It also had high cleansing effect and did not show a quality change with temperature change and with time, showing superior stability.

Example 36

Treatment Gel

| Components | wt % |
|---|---|
| 1. Ethanol | 20.0 |
| 2. Alternating copolymer 3 | 0.5 |
| 3. Glyceryl triisooctanoate | 3.0 |
| 4. Stearoxy-modified silicone[1] | 2.0 |
| 5. Silicone composite powder[2] | 8.0 |
| 6. Carboxy vinyl polymer (1% aqueous solution) | 20.0 |
| 7. Triethanol amine | 0.2 |
| 8. Antiseptic | q.l. |
| 9. Perfume | q.l. |
| 10. Purified water | 46.3 |

[1]Stearoxy-modified silicone KF-7002 (from Shin-Etsu Chemical Co., Ltd.)
[2]Silicone composite powder: KSP-100 (from Shin-Etsu Chemical Co., Ltd.)

(Preparation Method)
Step 1 Components 1-5 were combined and dispersed.
Step 2 Components 6-8 and 10 were mixed to obtain a homogeneous mixture.
Step 3 The resulting mixture from the Step 1 was added to that from the Step 2, to which Component 8 was added to mix homogeneously.

The treatment gel thus obtained spread lightly on the skin, had a non-tacky and non-greasy touch, and left skin moisturized, hydrated and refreshed feeling. It also had high affinity with skin and did not show quality change with temperature change or with time, showing superior stability.

Example 37

Wash-Off Pack

| Components | wt % |
| --- | --- |
| 1. Dimethylpolysiloxane with a viscosity of 6 mm$^2$/sec) | 3.0 |
| 2. Alternating copolymer 2 | 2.0 |
| 3. Kaolin | 30.0 |
| 4. Carboxy vinylpolymer | 0.4 |
| 5. 1,3-butylene glycol | 10.0 |
| 6. Glycerin | 20.0 |
| 7. Triethanolamine | 0.4 |
| 8. Antiseptic | q.l. |
| 9. Perfume | q.l. |
| 10. Purified water | 34.2 |

(Preparation Method)

Step 1 Components 1, 2 and 8 were mixed.

Step 2 Components 4-7 and 10 were mixed homogeneously and then Component 3 was added to mix.

Step 3 To the resulting mixture from Step 2, that from Step 1 was added to emulsify, to which Component 9 was added to obtain a paste of wash-off pack.

The wash-off pack thus obtained spread lightly on the skin, was highly effective in washing the skin, and left skin moisturized, non-tacky, and smooth feels after washing off. It had good properties for use and superior stability.

Example 38

Deodorant

| Components | wt % |
| --- | --- |
| 1. Decamethylcyclopentasiloxane | 12.0 |
| 2. Dimethylpolysiloxane with a viscosity of 6 mm$^2$/sec) | 4.0 |
| 3. Alternating copolymer 4 | 1.0 |
| 4. Propylene glycol | 31.0 |
| 5. Triclosan | 0.1 |
| 6. Glycerin | 15.0 |
| 7. Antiseptic | q.l. |
| 8. Perfume | q.l. |
| 9. Purified water | 36.8 |

(Preparation Method)

Step 1: Components 1-3 were mixed.

Step 2: Components 5 was dissolved in Component 4, and then Components 6-9 were mixed.

Step 3: Under a vigorous stirring, the resulting mixture from Step 2 was added to the resulting mixture from Step 1 to emulsify.

Step 4: 65 parts by weight of the resulting mixture from Step 3 and 35 parts by weight of a propellant (a mixture of n-butane, isobutane, and propane) were put in an aerosol can to obtain a deodorant.

The deodorant thus obtained demonstrated no sagging when used at a high concentration and was non-tacky and light. It provided a long lasting effect, showing good properties for use.

Example 39

O/W/O Milky Lotion

| Components | wt % |
| --- | --- |
| 1. Cross-linked polyether-modified silicone[1] | 3.0 |
| 2. Alternating copolymer 5 | 1.0 |
| 3. Gryceryl trioctanoate | 14.0 |
| 4. Cross-linked alkyl-modified silicone compound[2] | 5.0 |
| 5. Sucrose monostearate | 3.0 |
| 6. Glycerin | 5.0 |
| 7. 1,3-butylene glycol | 5.0 |
| 8. Antiseptic | q.l. |
| 9. Purified water | 60.0 |
| 10. Macadamia nut oil | 2.0 |
| 11. Cetyl alcohol | 2.0 |
| 12. Perfume | q.l. |

[1]Cross-linked polyether-modified silicone: KSG-210 (from Shin-Etsu Co., Ltd.)
[2]Cross-linked alkyl-modified silicone compound: KSG-43 (from Shin-Etsu Co., Ltd.)

(Preparation Method)

Step 1 Components 1-4 were mixed homogeneously.

Step 2 Components 5-9 were mixed while heating to obtain a homogeneous mixture.

Step 3 Components 10-12 were mixed while heating.

Step 4 The resulting mixture from Step 3 was added to that from Step 2 while stirring to emulsify and cool.

Step 5 The resulting mixture from Step 4 was added to that from Step 1 while stirring to emulsify.

The milky lotion thus obtained spread lightly on the skin, had a non-tacky and non-greasy touch, and gave a transparent finish. The coverage wore long and it did not show quality change with temperature change or with time. It was a superior O/W/O type milky lotion with good properties for use and stability.

Example 40

O/W/O Type Liquid Foundation

| Components | wt % |
| --- | --- |
| 1. Cross-linked polyether-modified silicone[1] | 4.0 |
| 2. Alternating copolymer 4 | 1.0 |
| 3. Propylene glycol decanoate | 5.0 |
| 4. Isopropyl myristate | 5.0 |
| 5. Pigment | 10.0 |
| 6. Hydrogenated phospholipid from egg yolk | 1.0 |
| 7. Glycerin | 2.0 |
| 8. 1,3-butylene glycol | 10.0 |
| 9. Antiseptic | q.l. |
| 10. Purified water | 52.0 |
| 11. Squalane | 5.0 |
| 12. Cetyl alcohol | 5.0 |
| 13. Perfume | q.l. |

[1]Cross-linked polyether-modified silicone: KSG-210 (from Shin-Etsu Co., Ltd.)

(Preparation Method)

Step 1 Components 1-4 were mixed homogeneously.

Step 2 Components 5-10 were mixed while heating to obtain a homogeneous mixture.

Step 3 Components 11-13 were mixed while heating.

Step 4 The resulting mixture from Step 3 was added to that from Step 2 while stirring to emulsify and cool.

Step 5 The resulting mixture from Step 4 was added to that from Step 1 while stirring to emulsify.

The liquid foundation thus obtained spread lightly on the skin, had a non-tacky and non-greasy touch and gave a transparent finish. It gave a long lasting coverage and no quality change was observed with temperature change and with time. It was a superior O/W/O type liquid foundation with good properties for use and stability.

Example 41

W/O Type Cream

| Components | wt % |
|---|---|
| 1. Alkyl-modified crosslinked polyether-modified silicone[1] | 6.0 |
| 2. Liquid paraffins | 13.5 |
| 3. Macadamia nuts oil | 4.0 |
| 4. Alternating copolymer 5 | 1.5 |
| 5. Sodium citrate | 0.2 |
| 6. Propylene glycol | 8.0 |
| 7. Glycerol | 3.0 |
| 8. Antiseptics | q.l. |
| 9. Perfume | q.l. |
| 10. Purified water | 60.8 |

[1]Alkyl-modified crosslinked polyether-modified silicone: KSG-310, ex Shin-Etsu Co., Ltd.

(Preparation Procedures)

Step 1: Components 1 to 4 were mixed.

Step 2: Components 5 to 10 were mixed to dissolve and the resulting mixture was added to the mixture obtained in Step 1. The resulting mixture was emulsified.

The cream thus obtained was found to be non-tacky, non-oily, lightly extendable, to have an affinity the skin, cling to skin, gives shiny finish. It could also provide cool feeling for skin.

Example 42

W/O Type Cream

| Components | wt % |
|---|---|
| 1. Alkyl-modified crosslinked polyether-modified silicone[1] | 7.0 |
| 2. Liquid paraffins | 13.5 |
| 3. Macadamia nuts oil | 5.0 |
| 4. Alternating copolymer 5 | 0.5 |
| 5. Composite powder of hybrid silicone[2] | 3.0 |
| 6. Sodium citrate | 0.2 |
| 7. Propylene glycol | 8.0 |
| 8. Glycerol | 3.0 |
| 9. Antiseptics | q.l. |
| 10. Perfume | q.l. |
| 11. Purified water | 59.8 |

[1]Alkyl-modified crosslinked polyether-modified silicone: KSG-810, ex Shin-Etsu Co., Ltd.
[2]Composite powder of hybrid silicone; KSP-100 (from Shin-Etsu Co., Ltd.)

Preparation Method

Step 1: Components 1 to 5 were mixed.

Step 2: Components 6 to 11 were mixed to dissolve and the resulting mixture was added to the mixture obtained in Step 1. The resulting mixture was emulsified.

The cream thus obtained was found to be non-tacky, non-oily, lightly extendable, to have an affinity the skin, cling to skin, gives mat finish. It could also provide cool feeling for skin.

Example 43

O/W Type Cream

| Components | wt % |
|---|---|
| 1. Crosslinked dimethylpolysiloxane[1] | 8.0 |
| 2. Crosslinked methylphenylpolysiloxane[2] | 2.0 |
| 3. Isotridecyl isononanate | 5.0 |
| 4. Dipropylene glycol | 7.0 |
| 5. Glycerol | 5.0 |
| 6. Methylcellulose (2% aqueous solution)[3] | 7.0 |
| 7. Polyacrylamide emulsifier[4] | 2.0 |
| 8. Alternating copolymer 1 | 0.5 |
| 9. Guanine | 1.0 |
| 10. Antiseptics | q.l. |
| 11. Perfume | q.l. |
| 12. Purified water | 62.5 |

[1]Crosslinked dimethylpolysiloxane: KSG-16 (from Shin-Etsu Co., Ltd.
[2]Crosslinked methylphenylpolysiloxane: KSG-18 (from Shin-Etsu Co., Ltd.)
[3]Metylcellulose: Metolose SM-4000 (from Shin-Etsu Co., Ltd.)
[4]Polyacrylamide emulsifier: Sepigel (from SEPIC Co.)

(Preparation Method)

Step 1: Components 4 to 11 were mixed.

Step 2: Components 1 to 3 were mixed to dissolve and the resulting mixture was added to the mixture obtained in Step 1 to emulsify.

The cream thus obtained was found to have a fine texture, moisturized feel and be non-tacky, non-oily, lightly extendable, and cling to skin to gives a mat finish. It could also provide cool feeling for skin.

Example 44

W/O Cream

| Components | % |
|---|---|
| 1. Crosslinked polyglycerol-modified siloxane[1] | 7.0 |
| 2. Dimethylpolysiloxane (6 mm$^2$/sec, 25 degrees C.) | 10.0 |
| 3. Alternating copolymer 4 | 0.5 |
| 4. Dipropylene glycol | 10.0 |
| 5. Sodium citrate | 0.2 |
| 6. Ethanol | 5.0 |
| 7. Antiseptics | q.l. |
| 8. Perfume | q.l. |
| 9. Purified water | 67.8 |

[1]Crosslinked polyglycerol-modified siloxane: KSG-710 (from Shin-Etsu Co., Ltd.

(Preparation Method)

Step 1: Components 1 to 3 were mixed while heating.

Step 2: Components 4 to 10 were mixed to dissolve and the resulting mixture was added to the mixture obtained in Step 1 to emulsify.

The cream thus obtained was found to give non-tacky, non-oily feel. It extended lightly to give a moisturized feel. It clung to the skin to gives a cool feeling and mat finish.

Example 45

W/O Makeup Base

| Components | wt % |
|---|---|
| 1. Crosslinked polyether-modified siloxane[1] | 5.0 |
| 2. Crosslinked dimethylpolysiloxane[2] | 1.0 |
| 3. Alternating copolymer 4 | 0.5 |
| 4. Dimethylpolysiloxane (6 mm$^2$/sec, 25 degrees C.) | 6.0 |
| 5. Dimethylpolysiloxane (20 mm$^2$/sec, 25 degrees C.) | 2.0 |
| 6. Decamethylpenatsiloxane | 3.0 |
| 7. Titanium oxide dispersed in cyclopentasiloxane[3] | 10.0 |
| 8. Dipropylene glycol | 5.0 |
| 9. Sodium citrate | 0.2 |
| 10. Methylcellulose (2% aqueous solution)[4] | 2.5 |
| 11. Ethanol | 3.0 |
| 12. Antiseptics | q.l. |
| 13. Perfume | q.l. |
| 14. Purified water | 62.8 |

[1]Crosslinked polyether-modified siloxane: KSG-210 (from Shin-Etsu Co., Ltd.)
[2]Crosslinked dimethylpolysiloxane: KSG-15 (from Shin-Etsu Co., Ltd.)
[3]Titanium oxide dispersed in cyclopentasiloxane: SPD-15 (from Shin-Etsu Co., Ltd.)
[4]Metylcellulose: Metolose SM-4000 (from Shin-Etsu Co., Ltd.)

(Preparation Method)
Step 1: Components 1 to 7 were mixed while heating.
Step 2: Components 8 to 15 were mixed to dissolve and the resulting mixture was added to the mixture obtained in Step 1 to emulsify.

The cream thus obtained was found to be non-tacky, non-oily. It extended lightly, cling to skin to gives a cool feeling and mat finish. In addition, the applied cream have a UV protection effect and lasted long.

Example 46

O/W Type Cream

| Components | wt % |
|---|---|
| 1. Alkyl-crosslinked dimethylpolysiloxane[1] | 2.0 |
| 2. Crosslinked dimethylpolysiloxane[2] | 15.0 |
| 3. Decamethylpentasiloxane | 10.0 |
| 4. Dimethylpolysiloxane (6 mm$^2$/sec, 25 degrees C.) | 18.0 |
| 5. Alternating copolymer 1 | 0.7 |
| 6. Propylene glycol | 3.0 |
| 7. Polyacrylamide mixture[3] | 0.8 |
| 8. Xanthan gum (2% aqueous solution) | 8.0 |
| 9. Antiseptics | q.l. |
| 10. Perfume | q.l. |
| 1. Purified water | 42.5 |

[1]Alkyl-crosslinked dimethylpolysiloxane: KSG-43 (from Shin-Etsu Co., Ltd.
[2]Crosslinked dimethylpolysiloxane: KSG-16 (from Shin-Etsu Co., Ltd.)
[3]Polyacrylamide mixture: Sepigel 305 (from SEPIC Co.)

(Preparation Method)
Step 1: Components 1 to 4 were mixed while heating.
Step 2: Components 8 to 15 were mixed to dissolve and the resulting mixture was added to the mixture obtained in Step 1 to emulsify.

The cream thus obtained had a fine texture and extended lightly on the skin to give an non-tacky, non-oily, and moisturized feel. The applied cream lasted long. The quality of the cream did not change with temperature change and with time.

Example 47

Powder Foundation

| Components | wt % |
|---|---|
| 1. Vaseline | 2.5 |
| 2. Squalane | 3.0 |
| 3. Alternating copolymer 5 | 0.5 |
| 4. Glyceryl trioctanoate | 2.0 |
| 5. Mica treated with silicone | 40.0 |
| 6. Talc treated with silicone | Balance |
| 7. Titanium oxide treated with silicone | 10.0 |
| 8. Titanium oxide fine powder treated with silicone | 5.0 |
| 9. Barium oxide treated with silicone | 10.0 |
| 10. Pigment | q.l. |
| 11. Phenyl-modified hybrid silicone composite powder[1] | 2.0 |
| 12. Silicone powder[2] | 2.5 |
| 13. Antiseptics | q.l. |
| 14. Perfume | q.l. |

[1]Phenyl-modified hybrid silicone composite powder: KSP-300 (from Shin-Etsu Co., Ltd.)
[2]Silicone powder: KMP-590 (from Shin-Etsu Co., Ltd.)

(Preparation Procedures)
Step 1: Components 4 to 13 were mixed to be homogeneous.
Step 2: Components 1 to 3 were mixed and the resulting mixture was added to the mixture obtained in Step 1.
Step 3: To the mixture obtained in Step 2, component 14 was added and the resulting mixture was pressed in a mold to prepare a foundation.

The foundation thus obtained was found to have a fine texture with non-tacky touch and spread lightly. It had an affinity to the skin and clung to the skin to give a shiny finish.

Example 48

Cream Foundation

| Components | wt % |
|---|---|
| 1. Crosslinked polyether-modified silicone | 5.0 |
| 2. Alternating copolymer 3 | 0.5 |
| 3. Glyceryl trioctanoate | 4.0 |
| 4. Dimethylpolysiloxane (6 mm$^2$/sec, 25 degrees C.) | 5.0 |
| 5. Decamethylpentasiloxane | 6.0 |
| 6. Phenyl-modified hybrid silicone composite powder[1] | 2.5 |
| 7. Pigment | 8.0 |
| 9. Acrylic silicone resin[2] | 5.0 |
| 9. Dipropylene glycol | 5.0 |
| 10. Sodium citrate | 0.2 |
| 11. Antiseptics | q.l. |
| 12. Perfume | q.l. |
| 13. Purified water | 59.3 |

[1]Phenyl-modified hybrid silicone composite powder: KSP-200 (from Shin-Etsu Co., Ltd.)
[2]Acrylic silicone resin: KP-575 (from Shin-Etsu Co., Ltd.)

(Preparation Procedures)
Step 1: Components 1 to 6 were mixed while heating.
Step 2: Components 9 to 13 were mixed to dissolve and the resulting mixture was added to the mixture obtained in Step 1.
Step 3: To the mixture obtained in Step 2, components 7 and 8 were added and homogeneously mixed.

The cream foundation thus obtained was found to have an non-tacky touch and spread lightly. It had an affinity to the skin and clung to the skin to give a mat finish.

Example 49

W/O Compact Foundation

| Components | wt % |
|---|---|
| 1. Ceresin wax | 5.5 |
| 2. Microcrystalline wax | 1.0 |
| 3. Liquid paraffin | 3.0 |
| 4. Alkyl-crosslinked dimethylpolysiloxane[1] | 9.0 |
| 5. Polypropylene glycol Dicaprate | 3.0 |
| 6. Alternating copolymer 5 | 1.0 |
| 7. Dimethylpolysiloxane (6 $mm^2$/sec, 25 degrees C.) | 15.5 |
| 8. Titanium oxide treated with oil | 10.0 |
| 9. Pigment | q.l. |
| 10. Lecithin | 0.3 |
| 11. Polyoxyethylene sorbitan monooleate | 0.5 |
| 12. Dipropylene glycol | 8.0 |
| 13. Sodium citrate | 0.2 |
| 14. Purified water | Balance |

[1] Alkyl-crosslinked dimethylpolysiloxane: KSG-310 (from Shin-Etsu Co., Ltd.

(Preparation Method)

Step 1: Components 1 to 7 were mixed while heating.

Step 2: Components 8 to 12 were homogeneously mixed.

Step 3: Components 13 and 14 were mixed, to which the mixture obtained in Step 2 was added and heated to be homogeneous.

Step 4: The mixture obtained in Step 3 and the mixture obtained in Step 2 were added and emulsified.

The compact foundation thus obtained was found to be non-tacky, non-oily in spite of a relatively large amount of oily components. It extended lightly, clung to the skin to gives a cool feeling. The applied foundation lasted long.

Example 50

Eye Shadow

| Components | wt % |
|---|---|
| 1. Cerisite | 40.0 |
| 2. Mica | 10.0 |
| 3. Talc | Balance |
| 4. Titanium dioxide | 10.0 |
| 5. Titanium dioxide fine powder | 5.0 |
| 6. Magnesium stearate | 3.0 |
| 7. Pigment | q.l. |
| 8. Octyldodecanol | 3.0 |
| 9. Dimethylpolysiloxane (6 $mm^2$/sec, 25 degrees C.) | 4.0 |
| 10. Alternating copolymer 5 | 6.0 |
| 11. Antiseptics | q.l. |
| 12. Perfume | q.l. |

(Preparation Method)

Step 1: Components 8 to 11 were mixed while heating.

Step 2: The mixture of components 1 to 7 were made to which the mixture obtained in Step 1 was added to make a homogeneous mixture.

The eye shadow thus obtained was found to be non-tacky, non-oily. It spreads lightly on the skin, clung to the skin to give a shiny finish. The applied eye shadow lasted long.

Example 51

Powder Eyebrow

| Components | wt % |
|---|---|
| 1. Vaseline | 2.5 |
| 2. Dimethylpolysiloxane (6 $mm^2$/sec, 25 degrees C.) | 1.5 |
| 3. Alternating copolymer 5 | 0.5 |
| 4. Glyceryl trioctanoate | 4.0 |
| 5. Mica treated with silicone | 40.0 |
| 6. Talc treated with silicone | Balance |
| 7. Titanium oxide treated with silicone | 10.0 |
| 8. Barium oxide treated with silicone | 15.0 |
| 9. Pigment treated with silicone | q.l. |
| 9. Hybrid silicone composite powder[1] | 1.5 |
| 12. Spherical polymethylsylsesquioxane powder[2] | 2.5 |
| 13. Antiseptics | q.l. |
| 14. Perfume | q.l. |

[1] Phenyl-modified hybrid silicone composite powder: KSP-100 (from Shin-Etsu Co., Ltd.)
[2] Spherical polymethylsylsesquioxane powder: KMP-500 (from Shin-Etsu Co., Ltd.)

(Preparation Procedures)

Step 1: Components 5 to 12 were mixed to make a homogeneous mixture.

Step 2: Components 1 to 3 were mixed and the resulting mixture was added to the mixture obtained in Step 1.

Step 3: To the mixture obtained in Step 2, component 13 was added and the resulting mixture was pressed in a mold to prepare a powder eyebrow.

The eyebrow thus obtained was found to be non-tacky. It spread lightly and clung to the skin to give a shiny finish. The applied eyebrow lasted long.

Example 52

Hair Cream

| Components | wt % |
|---|---|
| 1. Alternating copolymer 4 | 2.0 |
| 2. Dimethylpolysiloxane (6 $mm^2$/sec, 25 degrees C.) | 5.0 |
| 3. Decamethylcyclopentasiloxane | 8.0 |
| 4. Stearyltrimethylammonium chloride | 1.5 |
| 5. Glycerol | 3.0 |
| 6. Propylene glycol | 5.0 |
| 8. Hydroxyethyl cellulose | 0.2 |
| 9. Antiseptics | q.l. |
| 10. Perfume | q.l. |
| 11. Purified water | 75.3 |

(Preparation Procedures)

Step 1: Components 1 to 3 were mixed while heating.

Step 2: Components 4 to 8 and 10 were mixed to make a homogeneous mixture.

Step 3: To the mixture obtained in Step 2, the mixture obtained in Step 1 was added to make an emulsion. After cooling the emulsion, component 9 was added.

The hair cream thus obtained spread lightly to make the hair soft, smooth, easy to arrange, moisturized and shiny.

Example 53

Conditioning Mousse

| Components | wt % |
| --- | --- |
| 1. Alternating copolymer 3 | 0.5 |
| 2. Dimethylpolysiloxane (6 mm$^2$/sec, 25 degrees C.) | 2.0 |
| 3. Crosslinked dimethylpolysiloxane[1] | 0.5 |
| 4. Glyceryl trioctanoate | 1.5 |
| 5. Glycerol | 3.0 |
| 6. Stearyldimethylbenzylammonium chloride | 0.5 |
| 7. Polyoxyethylene hardened castor oil | 0.5 |
| 8. Ethanol | 7.0 |
| 9. Antiseptics | q.l. |
| 10. Perfume | q.l. |
| 11. Purified water | 75.3 |
| 12. Liquified petroleum gas | 5.0 |

[1]Crosslinked dimethylpolysiloxane: KSG-16 (from Shin-Etsu Co., Ltd.)

(Preparation Procedures)

Step 1: Components 1 to 4 were mixed while heating.

Step 2: Components 5 to 9 and 11 were mixed to make a homogeneous mixture.

Step 3: To the mixture obtained in Step 2, the mixture obtained in Step 1 was added to make an emulsion. After cooling the emulsion, component 10 was added.

Step 4: The mixture obtained in Step 3 was packed in a can containing aerosol.

The mousse thus obtained gave moisturized, soft, smooth and non-greasy touch. It had an affinity to the hair and clung to the hair to give mat finish.

Example 54

W/O Type Antiperspirant

| Components | wt % |
| --- | --- |
| 1. Crosslinked polyether modified silicone[1] | 8.0 |
| 2. Alternating copolymer 3 | 1.0 |
| 3. Decamethylcyclopentasiloxane | 7.0 |
| 4. Glyceryl trioctanoate | 8.0 |
| 5. 1,3-butylene glycol | 5.0 |
| 6. Sodium citrate | 0.2 |
| 7. Aluminum cholohydrate | 20.0 |
| 8. Perfume | q.l. |
| 9. Purified water | 50.8 |

[1]Crosslinked polyether modified silicone: KSG-210 (from Shin-Etsu Co., Ltd.)

(Preparation Procedures)

Step 1: Components 1 to 4 were mixed while heating.

Step 2: A mixture of Components 5,6, and 9 were made to which components 7 and 8 were added and dissolved.

Step 3: To the mixture obtained in Step 2, the mixture obtained in Step 1 was added to make an emulsion.

The antiperspirant thus obtained spread lightly to give refreshed, cool, non-tacky, and non-greasy touch. It did not change with time or temperature.

Example 55

W/O Type UV Cut Cream

| Components | wt % |
| --- | --- |
| 1. Silicone treated zinc oxide | 20.0 |
| 2. Acrylic silicone resin[1] | 12.0 |
| 3. Decamethylcyclopentasiloxane | 20.0 |
| 4. Glyceryl trioctanoate | 3.0 |
| 5. Crosslinked polyether modified silicone[2] | 7.0 |
| 6. Polyether modified silicone[3] | 1.0 |
| 7. Alkyl/polyether-modified silicone[4] | 0.5 |
| 8. Alternating copolymer 5 | 0.5 |
| 9. Methoxy octylcinnamete | 6.0 |
| 10. Sodium citrate | 0.2 |
| 11. Dipropylene glycol | 3.0 |
| 12. Antiseptics | q.l. |
| 13. Perfume | q.l. |
| 14. Purified water | 26.8 |

[1]Acrylic silicone resin: KP-545 (from Shin-Etsu Co., Ltd.)
[2]Crosslinked polyether modified silicone: KSG-210 (from Shin-Etsu Co., Ltd.)
[3]Polyether modified silicone: KF-6017 (from Shin-Etsu Co., Ltd.)
[4]Alkyl/polyether-modified silicone: KF-6026 (from Shin-Etsu Co., Ltd.)

(Preparation Procedures)

Step 1: A part of component 1 and components 4 to 9 were mixed while heating.

Step 2: A mixture of components 10 to 12 and 14 were made which mixture was added to the mixture obtained in Step 1 to make an emulsion.

Step 3: To the emulsion obtained in Step 2, components 1,2, the rest of component 3 and component 13 were added to make a homogeneous mixture.

The UV cut cream thus obtained spread lightly to give refreshed, cool, non-tacky touch. It gave a transparent finish which lasted long. In addition, it did not change with time or temperature.

Example 56

W/O Type UV Cut Milky Lotion

| Components | wt % |
| --- | --- |
| 1. Dimethylpolysiloxane (6 mm$^2$/sec, 25 degrees C.) | 5.0 |
| 2. Glyceryl trioctanoate | 2.0 |
| 3. Crosslinked polyglycerol-modified silicone[1] | 6.0 |
| 4. Polyglyceryl-3 Polydimethylsiloxyethyl Dimethicone[2] | 0.5 |
| 5. Alternating copolymer 3 | 0.5 |
| 6. Titanium dioxide dispersed in decamethylcyclopentasiloxane[3] | 30.0 |
| 7. Zinc oxide dispersed in decamethylcyclopentasiloxane[4] | 30.0 |
| 8. Dipropylene glycol | 3.0 |
| 9. Sodium citrate | 0.2 |
| 10. Antiseptics | q.l. |
| 11. Perfume | q.l. |
| 12. Purified water | 22.8 |

[1]Crosslinked polyglycerol-modified silicone: KSG-710 (from Shin-Etsu Co., Ltd.)
[2]Polyglyceryl-3 Polydimethylsiloxyethyl Dimethicone: KF-6104 (from Shin-Etsu Co., Ltd.)
[3]Titanium dioxide dispersed in decamethylcyclopentasiloxane: SPD-T5 (from Shin-Etsu Co., Ltd.)
[4]Zinc oxide dispersed in decamethylcyclopentasiloxane: SPD-Z5 (from Shin-Etsu Co., Ltd.)

(Preparation Procedures)
Step 1: Components 1 to 5 were mixed while heating.
Step 2: A mixture of components 8 to 10 and 12 were made which mixture was added to the mixture obtained in Step 1 to make an emulsion by stirring.
Step 3: To the emulsion obtained in Step 2, components 6,7, and 11 were added to make a homogeneous mixture.

The UV cut milky lotion thus obtained spread lightly to give refreshed, non-tacky and non-greasy touch. It gave a transparent finish which lasted long. In addition, it did not change with time or temperature.

Example 57

W/O/W Type Cream

| Components | wt % |
| --- | --- |
| 1. Cetyl isooctanoate | 5.0 |
| 2. Crosslinked polyether-modified silicone[1] | 6.0 |
| 3. Alternating copolymer 4 | 0.5 |
| 4. Decamethylcyclopentasiloxane | 4.5 |
| 5. Mthylglucose dioleate | 1.5 |
| 6. Isohexadecane | 3.5 |
| 7. Magnesium sulfate | 0.5 |
| 8. Propylene glycol | 5.0 |
| 9. Purified water | 39.5 |
| 10. Cetylalcohol | 1.0 |
| 11. PEG-10 Soya seterol | 2.0 |
| 12. Antiseptics | q.l. |
| 13. Perfume | q.l. |
| 14. Purified water | 31.0 |

[1] Crosslinked polyether-modified silicone: KSG-210 (from Shin-Etsu Co., Ltd.)

(Preparation Procedures)
Step 1: Components 7 to 9 were mixed.
Step 2: A mixture of components 1 to 6 were made which mixture was added to the mixture obtained in Step 1 to make an emulsion by stirring.
Step 3: A mixture of components 10 to 12 and 14 were made to which the emulsion obtained in Step 2 was added to make an emulsion.
Step 4: To the emulsion obtained in Step 3, component 13 was added to make a homogeneous mixture.

The cream thus obtained spread lightly to give refreshed, non-tacky and non-greasy touch. It gave a transparent finish which lasted long. In addition, it did not change with time or temperature.

Example 58

W/O Type Cream

| Components | wt % |
| --- | --- |
| 1. Alkyl crosslinked polyglycerol-modified silicone[1] | 3.0 |
| 2. Alkyl Crosslinked dimethylpolysiloxane[2] | 2.0 |
| 3. Alkyl/polyclycerol-modified silicone[3] | 0.5 |
| 4. Alternating copolymer 5 | 0.5 |
| 5. Squalane | 14.0 |
| 6. Macadamia nuts oil | 3.0 |
| 7. Hybrid silicone composite powder[4] | 2.0 |
| 8. Sodium citrate | 0.2 |
| 9. Sodium chloride | 0.5 |
| 10. Dipropylene glycol | 8.0 |
| 11. Glycerol | 4.0 |
| 12. Antiseptics | q.l. |
| 13. Perfume | q.l. |
| 14. Purified water | 62.3 |

[1] Alkyl crosslinked polyglycerol-modified silicone: KSG-840, ex Shin-Etsu Co., Ltd.
[2] Alkyl Crosslinked dimethylpolysiloxane; KSG-44 (from Shin-Etsu Co., Ltd.)
[3] Alkyl/polyclycerol-modified silicone: KF-6105 (from Shin-Etsu Co., Ltd.)
[4] Hybrid silicone composite powder: KSP-100 (from Shin-Etsu Co., Ltd.)

(Preparation Procedures)
Step 1: Components 1 to 7 were mixed.
Step 2: Components 8 to 14 were mixed.
Step 3: The mixture obtained in Step 2 was added to the mixture obtained in Step 1 and emulsified by stirring.

The cream thus obtained was found to be non-tacky, non-oily, and spread lightly to give refreshed feeling. It clung to skin to give mat finish.

Example 59

W/O Type Cream

| Components | wt % |
| --- | --- |
| 1. Crosslinked polyglycerol-modified silicone[1] | 5.0 |
| 2. Dimethylpolysiloxane (6 mm$^2$/sec, 25 degrees C.) | 11.5 |
| 3. Alternating copolymer 4 | 0.5 |
| 4. Dipropylene glycol | 10.0 |
| 5. Sodium citrate | 0.2 |
| 6. Sodium chloride | 0.5 |
| 7. Ethanol | 5.0 |
| 8. Antiseptics | q.l. |
| 9. Perfume | q.l. |
| 10. Purified water | 67.3 |

[1] Crosslinked polyglycerol-modified silicone: KSG-710 (from Shin-Etsu Co., Ltd.)

(Preparation Procedures)
Step 1: Components 1 to 3 were mixed.
Step 2: Components 4 to 10 were mixed which was then added to the mixture obtained in Step 1 to make an emulsion by stirring.

The cream thus obtained spread lightly to give refreshed, non-tacky and non-greasy touch. It had an excellent affinity to the skin to moisturized the skin.

Example 60

W/O Type Milky Lotion

| Components | wt % |
| --- | --- |
| 1. Polyether-modified silicone[1] | 1.5 |
| 2. Alternating copolymer 3 | 0.5 |
| 3. Dextrin fatty acid ester[2] | 0.2 |
| 4. Stearic acid ester of fructo-oligosaccharide[3] | 1.8 |
| 5. Dimethylpolysiloxane (6 mm$^2$/sec, 25 degrees C.) | 6.0 |
| 6. Decamethylcyclopentapolysiloxane | 22.0 |
| 7. 1,3-butylene glycol | 7.0 |

| Components | wt % |
|---|---|
| 8. Sodium citrate | 0.2 |
| 9. Ethanol | 5.0 |
| 10. Antiseptics | q.l. |
| 11. Perfume | q.l. |
| 12. Purified water | 55.8 |

[1] Polyether-modified silicone: KF-6019 (from Shin-Etsu Co., Ltd.)
[2] Dextrin fatty acid ester: Rheopearl TT, ex Chiba Seifun Co., Ltd.
[3] Stearic acid ester of fructo-oligosaccharide: Rheopearl ISK, ex Chiba Seifun Co., Ltd.

(Preparation Procedures)
Step 1: Components 1 to 6 were mixed while heating.
Step 2: A mixture of components 7 to 12 were made which mixture was added to the mixture obtained in Step 1 to make an emulsion by stirring.

The milky lotion thus obtained was non-tacky and non-greasy. It spread lightly and clung to the skin to give refreshed and moisturized feel.

Example 61

O/W Cream

| Components | wt % |
|---|---|
| 1. Alternating copolymer 1 | 2.0 |
| 2. Crosslinked dimethylpolysiloxane[1] | 28.0 |
| 3. Decamethylcyclopentasiloxane | 10.0 |
| 4. Dimethylpolysiloxane (6 mm$^2$/sec, 25 degrees C.) | 5.0 |
| 5. Polyglycerol-modified silicone[2] | 0.7 |
| 6. 1,3-butylene glycol | 3.0 |
| 7. Polyacrylamide type mixture[3] | 0.8 |
| 8. Polyoxyethylene hardened castor oil | 0.5 |
| 9. Water soluble polymer (5% aqueous solution)[4] | 10.0 |
| 10. Sodium chloride | 0.1 |
| 11. Antiseptics | q.l. |
| 10. Perfume | q.l. |
| 11. Purified water | 39.9 |

[1] Crosslinked dimethylpolysiloxane: KSG-16 (from Shin-Etsu Co., Ltd.)
[2] Polyglycerol-modified silicone: KF-6100 (from Shin-Etsu Co., Ltd.)
[3] Polyacrylamide type mixture: Sepigel 305 (from SEPIC Co., Ltd.)
[4] Water soluble polymer: Alistofex AVC, ex Client Co., Ltd. (Preparation Procedures)

Step 1: Components 1 to 4 were mixed.
Step 2: Components 5 to 13 were mixed to make a solution.
Step 3: To the solution obtained in Step 2, the mixture obtained in Step 1 was added to make an emulsion by stirring.

The cream thus obtained had fine texture and spread lightly on the skin to give non-tacky, non-greasy, moisturized and refreshed feeling. The applied cream lasted long. The cream did not change with time or temperature.

Example 62

Lipstick

| Components | wt % |
|---|---|
| 1. Candelilla wax | 4.0 |
| 2. Polyethylene wax | 2.0 |
| 3. Microcrystalline wax | 3.0 |
| 4. Ceresin | 7.0 |
| 4. Acrylate/dimethylsilicone copolymer[1] | 15.0 |
| 5. Alternating copolymer 5 | 0.5 |
| 6. Polyglycerol-modified silicone[2] | 2.0 |
| 7. Hydrogenated polyisobutene | 15.0 |
| 8. Maleic acid diisostearate | 12.0 |
| 9. Macadamia nut oil | 30.0 |
| 10. Isotridecyl isononanate | 10.0 |
| 11. Glyceryl triisostearate | 4.0 |
| 12. Pigment | q.l. |
| 13. Antiseptic | q.l. |
| 16. Perfume | q.l. |

[1] Acrylate/dimethylsilicone copolymer: KP-561P (from Shin-Etsu Co., Ltd.)
[2] Polyglycerol-modified silicone: KF-6105 (from Shin-Etsu Co., Ltd.)

(Preparation Procedures)
Step 1 Components 1-10 and 13 were mixed while heating to melt.
Step 2 Components 11 and 12 was mixed to make a homogeneous mixture.
Step 3: Component 14 and the mixture obtained in Step 2 were added to the melt obtained in Step 1 to make homogeneous mixture which was molded.

The lipstick thus obtained spread lightly on the lips to give a non-tacky, non-powdery and moisturized feel. The applied lipstick had good water resistance and water repellency and lasted long.

Example 63

Liquid Foundation

| Components | wt % |
|---|---|
| 1. Crosslinked polyether-modified silicone[1] | 3.0 |
| 2. Alternating copolymer 4 | 0.5 |
| 3. Crosslinked dimethylpolysiloxane[2] | 5.0 |
| 4. Polyether-modified silicone[3] | 1.0 |
| 5. Clay minerals modified with organic compounds[4] | 1.2 |
| 6. Glyceryl trioctanoate | 5.0 |
| 7. Dimethylpolysiloxane (6 mm$^2$/sec, 25 degrees C.) | 6.5 |
| 8. Decamethylcyclopentasiloxane | 21.6 |
| 9. Pigment treated with organopolysiloxane[5] | 10.0 |
| 10. Acrylic silicone resin[6] | 1.5 |
| 11. Dipropylene glycol | 5.0 |
| 12. Sodium citrate | 0.2 |
| 13. Antiseptic | q.l. |
| 14. Perfume | q.l. |
| 15. Purified water | 59.3 |

[1] Crosslinked polyether-modified silicone: KSG-210 (from Shin-Etsu Chemical Co., Ltd.)
[2] Crosslinked dimethylpolysiloxane: KSG-15 (from Shin-Etsu Chemical Co., Ltd.)
[3] Polyether-modified silicone: KF-6028 (from Shin-Etsu Chemical Co., Ltd.)
[4] Clay minerals modified with organic compounds: Bentone 38, ex NL Industry Co., Ltd.
[5] Pigment treated with organopolysiloxane: KF-9909, ex Shin-Etsu Chemical Co., Ltd.
[6] Acrylic silicone resin: KP-575, ex Shin-Etsu Chemical Co., Ltd.

(Preparation Procedures)
Step 1: Components 1 to 6, a part of component 7 and 8 were mixed.
Step 2: The rest of component 7 and 8, components 9, and 10 were mixed.
Step 3: Components 11 to 15 were mixed to make a solution.
Step 4: The solution obtained in Step 3 was added to the mixture obtained in Step 1 to make an emulsion by stirring.

Step 5: The mixture obtained in Step 2 was added to the emulsion obtained in Step 4 to make a homogeneous mixture.

The foundation thus obtained was non-tacky and spread lightly on the skin to give a mat and stable finish clung to the skin.

Example 64

Creamy Eye Shadow

| Components | wt % |
|---|---|
| 1. Acrylate/dimethylsilicone copolymer[1] | 10.0 |
| 2. Acrylate/dimethylsilicone copolymer[2] | 2.0 |
| 3. Alternating copolymer 4 | 0.3 |
| 4. Polyglycerol-modified silicone[3] | 1.5 |
| 5. Decamethylcyclopentasiloxane | 20.0 |
| 6. Clay minerals modified with organic compounds[4] | 1.2 |
| 7. Cetyl isooctanoate | 3.0 |
| 8. Polyamide | 3.0 |
| 9. Talc | 4.0 |
| 10. Pigment treated with acrylic silicone resin[5] | 20.0 |
| 11. Ethanol | 5.0 |
| 12. Purified water | 30.0 |

[1] Acrylate/dimethylsilicone copolymer: KP-545, ex Shin-Etsu Chemical Co., Ltd.
[2] Acrylate/dimethylsilicone copolymer: KP-561P, ex Shin-Etsu Chemical Co., Ltd.
[3] Polyglycerol-modified silicone: KF-6105, ex Shin-Etsu Chemical Co., Ltd.
[4] Clay minerals modified with organic compounds: Bentone 38, ex NL Industry Co., Ltd.
[5] Pigment treated with acrylic silicone resin: KP-574, ex Shin-Etsu Chemical Co., Ltd.

(Preparation Method)

Step 1: Components 1 to 10 were mixed.

Step 2: A mixture of components 10 and 11 was made which was added to the mixture obtained in Step 1 to make a homogeneous mixture.

The eye shadow thus obtained was non-tacky and spread lightly on the skin to give a shiny finish which clung to the skin and lasted long.

Example 65

Wrinkle Cover Cream

| Components | wt % |
|---|---|
| 1. Cross linked polyether-modified silicone[1] | 5.0 |
| 2. Crosslinked dimetylpolysiloxane[2] | 55.0 |
| 3. Crosslinked dimetylpolysiloxane[3] | 15.0 |
| 4. Alternating copolymer 2 | 2.0 |
| 5. Decamethylcyclopentasiloxane | 13.0 |
| 6. Hybrid silicone composite powder[4] | 8.0 |
| 7. Spherical polymethylsylsesquioxane powder[5] | 2.0 |

[1] Crosslinked polyether-modified silicone: KSG-210 (from Shin-Etsu Co., Ltd.)
[2] Crosslinked dimetylpolysiloxane: KSG-15 (from Shin-Etsu Co., Ltd.)
[3] Crosslinked dimetylpolysiloxane: KSG-16 (from Shin-Etsu Co., Ltd.)
[4] Hybrid silicone composite powder: KSP-100 (from Shin-Etsu Co., Ltd.)
[5] Spherical polymethylsylsesquioxane powder: KMP-590 (from Shin-Etsu Co., Ltd.)

(Preparation Procedures)

Step 1: Components 1 to 7 were mixed to make a homogeneous mixture.

The cream thus obtained was non-tacky and non-greasy. It gave a moisturized, mat and stable finish.

INDUSTRIAL APPLICABILITY

The organopolysiloxane/polyglycerol alternating copolymer of the present invention is clear and compatible with conventional oil agents. It is a good emulsifier, too, to give a stable emulsion. A cosmetic comprising the copolymer has good affinity to the skin to give a non-tacky and non-greasy touch. The applied cosmetic is durable and has a shiny finish of an expensive-looking.

The invention claimed is:

1. An alternating copolymer comprising 2 to 100 repeating units (AB), wherein (A) is an α,ω-organohydrogensiloxane residue (A) and (B) a glycerol derivative residue having 1 to 11 hydroxyl groups, each repeating unit (AB) being represented by the following formula (1):

$$\left[ \left( SiO \right)_a (SiO)_b - Si \right) \left( Q - G - Q \right) \right] \quad (1)$$

wherein
  each $R^1$ may be the same or different and each $R^1$ is a group having 1 to 10 carbon atoms selected from the group consisting of alkyl, aryl, aralkyl, amino-substituted alkyl, and carboxyl-substituted alkyl groups, optionally substituted with halogen atoms,
  each $R^2$ may be the same or different and each $R^2$ is an alkyl group having 11 to 30 carbon atoms, optionally substituted with halogen atoms,
  Q is a divalent organic group having 3 to 20 carbon atoms and may comprise an ether bond and/or an ester bond,
  G is a mono- or poly-glycerol residue,
  a is an integer of from 2 to 100, and
  b is an integer of from 0 to 100.

2. The copolymer according to claim 1, wherein b is an integer of at least 1.

3. The copolymer according to claim 1, wherein G is represented by the following formula (2), $$-O\diagup\diagdown O\diagup\diagdown O\diagup_s \quad (2)$$
$$\quad\quad OH \quad\quad OH$$

wherein s is an integer of from 0 to 10.

4. The copolymer according to claim 1, wherein G is represented by the following formula (3), $$(3)$$

wherein t is an integer of from 0 to 10.

5. The copolymer according to claim 1, wherein G is represented by the following formula (4),

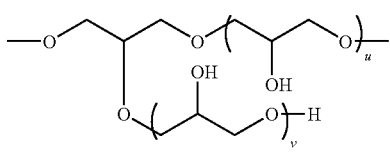

wherein u and v are integers of from 0 to 10.

6. The copolymer according to claim 1, wherein Q is a propylene group.

7. A cosmetic comprising the copolymer according to any one of claims 1 or 2 to 6.

8. The cosmetic according to claim 7, wherein the cosmetic is a skin-care cosmetic, a hair cosmetic, an antiperspirant, a makeup cosmetic, or a UV protecting cosmetic.

9. The cosmetic according to claim 7, wherein the cosmetic is in a form of liquid, milky lotion, cream, solid, paste, gel, powder, lamella, mousse, or spray.

10. An emulsifier comprising the copolymer according to any one of claims 1 or 2 to 6.

11. A process for preparing the copolymer according to any of claims 1 or 2 to 6 comprising a step of reacting α,ω-organohydrogensiloxane having an SiH bond at both terminals with a glycerol derivative having an aliphatic unsaturated bond at both terminals.

* * * * *